US012558175B2

(12) United States Patent     (10) Patent No.:   US 12,558,175 B2

Lau et al.                      (45) Date of Patent:     Feb. 24, 2026

---

(54) MULTI CATHETER METHOD OF PERFORMING A ROBOTIC NEUROVASCULAR PROCEDURE

(71) Applicant: Imperative Care, Inc., Campbell, CA (US)

(72) Inventors: Lilip Lau, Los Altos, CA (US); Robert Hitchcock, Los Gatos, CA (US); Kyle Bartholomew, Campbell, CA (US); David Gonzalez, Campbell, CA (US)

(73) Assignee: Imperative Care, Inc., Campbell, CA (US)

( * ) Notice: Subject to any disclaimer, the term of this patent is extended or adjusted under 35 U.S.C. 154(b) by 1040 days.

(21) Appl. No.: 17/527,456

(22) Filed: Nov. 16, 2021

(65)           Prior Publication Data

US 2023/0047098 A1     Feb. 16, 2023

Related U.S. Application Data

(60) Provisional application No. 63/232,444, filed on Aug. 12, 2021.

(51) Int. Cl.
*A61B 34/37*        (2016.01)
*A61B 5/00*         (2006.01)
            (Continued)

(52) U.S. Cl.
CPC ............ *A61B 34/37* (2016.02); *A61B 5/6852* (2013.01); *A61B 17/22* (2013.01); *A61B 34/30* (2016.02);
            (Continued)

(58) Field of Classification Search
CPC ....... A61B 34/37; A61B 5/6852; A61B 17/22; A61B 34/30; A61B 34/71;
            (Continued)

(56)           References Cited

U.S. PATENT DOCUMENTS 1,286,033 A    11/1918   Lambeth
3,605,750 A     9/1971   Sheridan et al.
          (Continued)

FOREIGN PATENT DOCUMENTS

AU          758458 B2     3/2003
AU      2006268156 B2     4/2012
          (Continued)

OTHER PUBLICATIONS

US 12,076,032 B1, 09/2024, Teigen et al. (withdrawn)
          (Continued)

*Primary Examiner* — Ariana Zimbouski
*Assistant Examiner* — Matthew Wrubleski
(74) *Attorney, Agent, or Firm* — Knobbe, Martens, Olson & Bear, LLP

(57)            ABSTRACT

A method of performing a neurovascular procedure includes the steps of providing an access assembly comprising a guidewire, access catheter and guide catheter; coupling the access assembly to a robotic drive system; and driving the access assembly to achieve supra-aortic vessel access. The guide wire and the access catheter are decoupled from the access assembly. A procedure assembly includes at least a guidewire and a procedure catheter. The procedure assembly is coupled to the robotic drive system; and used to perform a neurovascular procedure.

19 Claims, 14 Drawing Sheets

(51) Int. Cl.

| | |
|---|---|
| *A61B 17/22* | (2006.01) |
| *A61B 34/00* | (2016.01) |
| *A61B 34/30* | (2016.01) |
| *A61M 25/00* | (2006.01) |
| *A61M 25/01* | (2006.01) |
| *A61M 25/09* | (2006.01) |

(52) U.S. Cl.

CPC ......... *A61B 34/71* (2016.02); *A61M 25/0097* (2013.01); *A61M 25/0127* (2013.01); *A61M 25/09* (2013.01); *A61B 2017/22038* (2013.01); *A61B 2017/22079* (2013.01); *A61B 2034/301* (2016.02); *A61B 2034/715* (2016.02); *A61B 2562/0261* (2013.01); *A61M 25/002* (2013.01); *A61M 25/0113* (2013.01); *A61M 2205/3306* (2013.01); *A61M 2205/332* (2013.01); *A61M 2205/3331* (2013.01); *A61M 2205/3592* (2013.01); *A61M 2205/583* (2013.01)

(58) Field of Classification Search

CPC A61B 2017/22038; A61B 2017/22079; A61B 2034/301; A61B 2034/715; A61B 2562/0261; A61B 5/0215; A61B 5/14503; A61B 5/279; A61B 5/061; A61B 2017/00477; A61B 2017/00876; A61B 46/10; A61B 2090/064; A61B 50/33; A61B 50/30; A61M 25/0097; A61M 25/0127; A61M 25/09; A61M 25/002; A61M 25/0113; A61M 2205/3306; A61M 2205/332; A61M 2205/3331; A61M 2205/3592; A61M 2205/583

See application file for complete search history.

(56) References Cited

U.S. PATENT DOCUMENTS

| | | | |
|---|---|---|---|
| 3,884,242 A | 5/1975 | Bazell et al. | |
| 3,890,976 A | 6/1975 | Bazell et al. | |
| 3,965,901 A | 6/1976 | Penny et al. | |
| 4,030,503 A | 6/1977 | Clark, III | |
| 4,319,580 A | 3/1982 | Colley et al. | |
| 4,611,594 A | 9/1986 | Grayhack et al. | |
| 4,617,019 A | 10/1986 | Fecht et al. | |
| 4,619,274 A | 10/1986 | Morrison | |
| 4,628,168 A | 12/1986 | Nebergall et al. | |
| 4,762,129 A | 8/1988 | Bonzel | |
| 4,762,130 A | 8/1988 | Fogarty et al. | |
| 4,767,399 A | 8/1988 | Bollish | |
| 4,810,582 A | 3/1989 | Gould et al. | |
| 4,819,653 A | 4/1989 | Marks | |
| 4,844,064 A | 7/1989 | Thimsen et al. | |
| 4,898,575 A | 2/1990 | Fischell et al. | |
| 4,923,462 A | 5/1990 | Stevens | |
| 4,925,444 A | 5/1990 | Orkin | |
| 5,011,488 A | 4/1991 | Ginsburg | |
| 5,037,404 A | 8/1991 | Gold et al. | |
| 5,040,548 A | 8/1991 | Yock | |
| 5,103,827 A | 4/1992 | Smith | |
| 5,120,323 A | 6/1992 | Shockey et al. | |
| 5,131,391 A | 7/1992 | Sakai et al. | |
| 5,217,705 A | 6/1993 | Reno et al. | |
| 5,226,909 A | 7/1993 | Evans et al. | |
| 5,234,416 A | 8/1993 | Macaulay et al. | |
| 5,243,997 A | 9/1993 | Uflacker et al. | |
| 5,261,916 A | 11/1993 | Engelson et al. | |
| 5,290,247 A | 3/1994 | Crittenden | |
| 5,308,327 A | 5/1994 | Heaven et al. | |
| 5,328,472 A | 7/1994 | Steinke et al. | |
| 5,380,268 A | 1/1995 | Wheeler | |
| 5,413,560 A | 5/1995 | Solar | |
| 5,417,697 A | 5/1995 | Wilk et al. | |
| 5,423,846 A | 6/1995 | Fischell | |
| 5,439,445 A | 8/1995 | Kontos | |
| 5,441,051 A | 8/1995 | Hileman et al. | |
| 5,454,795 A | 10/1995 | Samson | |
| 5,466,222 A | 11/1995 | Ressemann et al. | |
| 5,474,563 A | 12/1995 | Myler et al. | |
| 5,527,292 A | 6/1996 | Adams et al. | |
| 5,549,119 A | 8/1996 | Solar | |
| 5,569,178 A | 10/1996 | Henley | |
| 5,569,277 A | 10/1996 | Evans et al. | |
| 5,591,187 A | 1/1997 | Dekel | |
| 5,638,818 A | 6/1997 | Diab et al. | |
| 5,643,254 A | 7/1997 | Scheldrup et al. | |
| 5,658,263 A | 8/1997 | Dang et al. | |
| 5,662,622 A | 9/1997 | Gore et al. | |
| 5,690,613 A | 11/1997 | Verbeek | |
| 5,695,483 A | 12/1997 | Samson | |
| 5,702,373 A | 12/1997 | Samson | |
| 5,713,848 A | 2/1998 | Dubrul et al. | |
| 5,766,191 A | 6/1998 | Trerotola | |
| 5,776,141 A | 7/1998 | Klein et al. | |
| 5,792,124 A | 8/1998 | Horrigan et al. | |
| 5,827,242 A | 10/1998 | Follmer et al. | |
| 5,843,103 A | 12/1998 | Wulfman | |
| 5,873,882 A | 2/1999 | Straub et al. | |
| 5,876,414 A | 3/1999 | Straub | |
| 5,882,333 A | 3/1999 | Schaer et al. | |
| 5,885,209 A | 3/1999 | Green | |
| 5,891,114 A | 4/1999 | Chien et al. | |
| 5,895,398 A | 4/1999 | Wensel et al. | |
| 5,899,892 A | 5/1999 | Mortier et al. | |
| 5,916,192 A | 6/1999 | Nita et al. | |
| 5,935,112 A | 8/1999 | Stevens | |
| 5,951,539 A | 9/1999 | Nita | |
| 5,989,208 A | 11/1999 | Nita | |
| 6,007,530 A | 12/1999 | Dornhofer et al. | |
| 6,056,837 A | 5/2000 | Lieber et al. | |
| 6,059,745 A | 5/2000 | Gelbfish | |
| 6,090,118 A | 7/2000 | McGuckin, Jr. | |
| 6,096,004 A * | 8/2000 | Meglan .................. A61B 34/74 604/95.01 |
| 6,152,909 A | 11/2000 | Bagaoisan et al. | |
| 6,159,230 A | 12/2000 | Samuels | |
| 6,165,163 A | 12/2000 | Chien et al. | |
| 6,165,199 A | 12/2000 | Barbut | |
| 6,171,295 B1 | 1/2001 | Garabedian et al. | |
| 6,179,859 B1 | 1/2001 | Bates et al. | |
| 6,197,014 B1 | 3/2001 | Samson et al. | |
| 6,206,852 B1 | 3/2001 | Lee | |
| 6,217,557 B1 | 4/2001 | Hakansson et al. | |
| 6,221,038 B1 | 4/2001 | Brisken | |
| 6,228,046 B1 | 5/2001 | Brisken | |
| 6,258,052 B1 | 7/2001 | Milo | |
| 6,267,783 B1 | 7/2001 | Letendre et al. | |
| 6,285,903 B1 | 9/2001 | Rosenthal et al. | |
| 6,355,027 B1 | 3/2002 | Le et al. | |
| 6,375,471 B1 | 4/2002 | Wendlandt et al. | |
| 6,394,976 B1 | 5/2002 | Winston et al. | |
| 6,400,971 B1 | 6/2002 | Firanov et al. | |
| 6,451,005 B1 | 9/2002 | Saitou et al. | |
| 6,451,036 B1 | 9/2002 | Heitzmann et al. | |
| 6,458,139 B1 | 10/2002 | Palmer et al. | |
| 6,468,219 B1 | 10/2002 | Njemanze | |
| 6,482,217 B1 | 11/2002 | Pintor et al. | |
| 6,511,492 B1 | 1/2003 | Rosenbluth et al. | |
| 6,520,934 B1 | 2/2003 | Lee et al. | |
| 6,524,303 B1 | 2/2003 | Garibaldi et al. | |
| 6,533,751 B2 | 3/2003 | Cragg et al. | |
| 6,554,820 B1 | 4/2003 | Wendlandt et al. | |
| 6,554,827 B2 | 4/2003 | Chandrasekaran et al. | |
| 6,558,377 B2 | 5/2003 | Lee et al. | |
| 6,569,148 B2 | 5/2003 | Bagaoisan et al. | |
| 6,579,246 B2 | 6/2003 | Jacobsen et al. | |
| 6,582,440 B1 | 6/2003 | Brumbach | |
| 6,591,472 B1 | 7/2003 | Noone et al. | |
| 6,638,268 B2 | 10/2003 | Niazi | |
| 6,663,613 B1 | 12/2003 | Evans et al. | |
| 6,666,874 B2 | 12/2003 | Heitzmann | |
| 6,669,670 B1 | 12/2003 | Muni et al. | |
| 6,719,717 B1 | 4/2004 | Johnson et al. | |

(56) References Cited

U.S. PATENT DOCUMENTS

| | | |
|---|---|---|
| 6,776,770 B1 | 8/2004 | Trerotola |
| 6,824,550 B1 | 11/2004 | Pintor et al. |
| 6,824,553 B1 | 11/2004 | Samson et al. |
| 6,929,633 B2 | 8/2005 | Evans et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas et al. |
| 7,037,267 B1 | 5/2006 | Lipson et al. |
| 7,104,979 B2 | 9/2006 | Jansen et al. |
| 7,112,298 B2 | 9/2006 | Kampa et al. |
| 7,172,620 B2 | 2/2007 | Gilson |
| 7,175,653 B2 | 2/2007 | Gaber |
| 7,192,433 B2 | 3/2007 | Osypka et al. |
| 7,207,980 B2 | 4/2007 | Christian et al. |
| 7,214,230 B2 | 5/2007 | Brock et al. |
| 7,223,274 B2 | 5/2007 | Vargas et al. |
| 7,229,461 B2 | 6/2007 | Chin et al. |
| 7,232,452 B2 | 6/2007 | Adams et al. |
| 7,235,088 B2 | 6/2007 | Pintor et al. |
| 7,306,585 B2 | 12/2007 | Ross |
| 7,309,334 B2 | 12/2007 | von Hoffmann |
| 7,331,967 B2 | 2/2008 | Lee et al. |
| 7,335,216 B2 | 2/2008 | Bender et al. |
| 7,379,790 B2 | 5/2008 | Toth et al. |
| 7,416,555 B2 | 8/2008 | Krivoruchko |
| 7,491,210 B2 | 2/2009 | Dubrul et al. |
| 7,507,229 B2 | 3/2009 | Hewitt et al. |
| 7,537,568 B2 | 5/2009 | Moehring |
| 7,556,611 B2 | 7/2009 | Kolenbrander et al. |
| 7,558,622 B2 | 7/2009 | Tran |
| 7,567,233 B2 | 7/2009 | Garibaldi et al. |
| 7,601,138 B2 | 10/2009 | Goebel et al. |
| 7,608,083 B2 | 10/2009 | Lee et al. |
| 7,615,042 B2 | 11/2009 | Beyar et al. |
| 7,678,100 B2 | 3/2010 | Chin et al. |
| 7,713,227 B2 | 5/2010 | Wholey et al. |
| 7,727,185 B2 | 6/2010 | Weitzner |
| 7,747,960 B2 | 6/2010 | Garibaldi et al. |
| 7,756,308 B2 | 7/2010 | Viswanathan |
| 7,761,133 B2 | 7/2010 | Viswanathan et al. |
| 7,763,196 B2 | 7/2010 | Goebel et al. |
| 7,766,871 B2 | 8/2010 | Hirszowicz et al. |
| 7,771,358 B2 | 8/2010 | Moehring et al. |
| 7,789,874 B2 | 9/2010 | Yu et al. |
| 7,803,136 B2 | 9/2010 | Schatz |
| D626,250 S | 10/2010 | Wenderow et al. |
| 7,818,076 B2 | 10/2010 | Viswanathan |
| 7,831,294 B2 | 11/2010 | Viswanathan |
| 7,837,692 B2 | 11/2010 | Mulholland et al. |
| 7,842,055 B2 | 11/2010 | Pintor et al. |
| 7,850,623 B2 | 12/2010 | Griffin et al. |
| 7,850,640 B2 | 12/2010 | Williams et al. |
| 7,850,642 B2 | 12/2010 | Moll et al. |
| 7,853,306 B2 | 12/2010 | Viswanathan et al. |
| 7,884,727 B2 | 2/2011 | Tran |
| 7,886,743 B2 | 2/2011 | Cooper et al. |
| 7,887,549 B2 | 2/2011 | Wenderow et al. |
| 7,905,891 B2 | 3/2011 | Self |
| 7,909,798 B2 | 3/2011 | Osypka |
| 7,931,659 B2 | 4/2011 | Bose et al. |
| 7,938,820 B2 | 5/2011 | Webster et al. |
| 7,951,243 B2 | 5/2011 | Boyle, Jr. et al. |
| 7,955,316 B2 | 6/2011 | Weitzner et al. |
| 7,955,344 B2 | 6/2011 | Finitsis |
| 7,955,345 B2 | 6/2011 | Kucharczyk et al. |
| 7,963,288 B2 | 6/2011 | Rosenberg et al. |
| 7,988,646 B2 | 8/2011 | Taber |
| 8,004,229 B2 | 8/2011 | Nowlin et al. |
| 8,021,326 B2 | 9/2011 | Moll et al. |
| 8,021,351 B2 | 9/2011 | Boldenow et al. |
| RE42,804 E | 10/2011 | Dedig et al. |
| 8,048,032 B2 | 11/2011 | Root et al. |
| 8,052,636 B2 | 11/2011 | Moll et al. |
| 8,057,497 B1 | 11/2011 | Raju et al. |
| 8,062,316 B2 | 11/2011 | Patel et al. |
| 8,070,694 B2 | 12/2011 | Galdonik et al. |
| 8,079,978 B2 | 12/2011 | Hirszowicz et al. |
| 8,083,753 B2 | 12/2011 | Solar et al. |
| 8,084,246 B2 | 12/2011 | Hoon et al. |
| 8,108,069 B2 | 1/2012 | Stahler et al. |
| 8,114,032 B2 | 2/2012 | Ferry et al. |
| 8,114,106 B2 | 2/2012 | Straub |
| 8,123,726 B2 | 2/2012 | Searfoss et al. |
| 8,123,769 B2 | 2/2012 | Osborne |
| 8,131,379 B2 | 3/2012 | Hauck |
| 8,137,317 B2 | 3/2012 | Osypka |
| 8,142,413 B2 | 3/2012 | Root et al. |
| 8,146,874 B2 | 4/2012 | Yu |
| 8,157,792 B2 | 4/2012 | Dolliver et al. |
| 8,165,684 B2 | 4/2012 | Putz et al. |
| 8,190,238 B2 | 5/2012 | Moll et al. |
| 8,211,023 B2 | 7/2012 | Swan et al. |
| 8,220,468 B2 | 7/2012 | Cooper et al. |
| 8,235,968 B2 | 8/2012 | Tremaglio |
| 8,242,972 B2 | 8/2012 | Garibaldi et al. |
| 8,244,824 B2 | 8/2012 | Garibaldi et al. |
| 8,246,641 B2 | 8/2012 | Osborne et al. |
| 8,257,302 B2 | 9/2012 | Beyar et al. |
| 8,262,671 B2 | 9/2012 | Osypka |
| 8,281,807 B2 | 10/2012 | Trombley et al. |
| 8,292,850 B2 | 10/2012 | Root et al. |
| 8,298,591 B2 | 10/2012 | Srivastava et al. |
| 8,307,693 B2 | 11/2012 | Uram et al. |
| D674,484 S | 1/2013 | Murphy et al. |
| 8,343,096 B2 | 1/2013 | Kirschenman et al. |
| 8,343,098 B2 | 1/2013 | Nystrom et al. |
| 8,361,095 B2 | 1/2013 | Osborne |
| 8,366,735 B2 | 2/2013 | Bose et al. |
| 8,377,077 B2 | 2/2013 | Reis |
| 8,382,739 B2 | 2/2013 | Walak et al. |
| 8,390,438 B2 | 3/2013 | Olson et al. |
| 8,394,078 B2 | 3/2013 | Torrance et al. |
| 8,399,871 B2 | 3/2013 | Beyar et al. |
| 8,403,909 B2 | 3/2013 | Spohn et al. |
| 8,403,912 B2 | 3/2013 | McFerran et al. |
| D680,645 S | 4/2013 | Murphy et al. |
| 8,409,172 B2 | 4/2013 | Moll et al. |
| 8,419,748 B2 | 4/2013 | Valaie |
| 8,449,566 B2 | 5/2013 | Finitsis |
| 8,460,312 B2 | 6/2013 | Bose et al. |
| 8,467,853 B2 | 6/2013 | Hunter et al. |
| D685,468 S | 7/2013 | Murphy et al. |
| 8,480,618 B2 | 7/2013 | Wenderow et al. |
| 8,480,697 B2 | 7/2013 | Kucharczyk et al. |
| 8,485,969 B2 | 7/2013 | Grayzel et al. |
| 8,498,691 B2 | 7/2013 | Moll et al. |
| 8,506,555 B2 | 8/2013 | Morales |
| 8,517,955 B2 | 8/2013 | Keast et al. |
| 8,521,331 B2 | 8/2013 | Itkowitz |
| 8,529,582 B2 | 9/2013 | Devengenzo et al. |
| 8,535,293 B2 | 9/2013 | Faherty et al. |
| 8,540,698 B2 | 9/2013 | Spohn et al. |
| 8,551,084 B2 | 10/2013 | Hauck et al. |
| 8,568,432 B2 | 10/2013 | Straub |
| 8,603,122 B2 | 12/2013 | Pokorney et al. |
| 8,608,754 B2 | 12/2013 | Wensel et al. |
| 8,608,761 B2 | 12/2013 | Osborne et al. |
| 8,609,426 B2 | 12/2013 | Silver |
| 8,613,730 B2 | 12/2013 | Hieb et al. |
| 8,617,102 B2 | 12/2013 | Moll et al. |
| 8,620,473 B2 | 12/2013 | Diolaiti et al. |
| 8,663,259 B2 | 3/2014 | Levine et al. |
| 8,671,817 B1 | 3/2014 | Bogusky |
| 8,672,880 B2 | 3/2014 | Cohen et al. |
| 8,682,411 B2 | 3/2014 | Kassab et al. |
| 8,684,953 B2 | 4/2014 | Cabiri |
| 8,684,962 B2 | 4/2014 | Kirschenman et al. |
| 8,684,963 B2 | 4/2014 | Qiu et al. |
| 8,694,157 B2 | 4/2014 | Wenderow et al. |
| 8,696,698 B2 | 4/2014 | Chomas et al. |
| 8,702,680 B2 | 4/2014 | Jimenez et al. |
| 8,702,724 B2 | 4/2014 | Olsen et al. |
| 8,725,249 B2 | 5/2014 | Bar-Yoseph et al. |

(56)                References Cited

U.S. PATENT DOCUMENTS

| 8,734,374 | B2 | 5/2014 | Aklog et al. |
| 8,740,840 | B2 | 6/2014 | Foley et al. |
| 8,747,358 | B2 | 6/2014 | Trombley et al. |
| 8,758,325 | B2 | 6/2014 | Webster et al. |
| 8,758,364 | B2 | 6/2014 | Eckhouse et al. |
| 8,764,779 | B2 | 7/2014 | Levine et al. |
| 8,784,441 | B2 | 7/2014 | Rosenbluth et al. |
| 8,790,297 | B2 | 7/2014 | Bromander et al. |
| 8,799,792 | B2 | 8/2014 | Garibaldi et al. |
| 8,800,881 | B2 | 8/2014 | Biset et al. |
| 8,801,661 | B2 | 8/2014 | Moll et al. |
| 8,806,359 | B2 | 8/2014 | Garibaldi et al. |
| 8,814,892 | B2 | 8/2014 | Galdonik et al. |
| 8,828,021 | B2 | 9/2014 | Wenderow et al. |
| 8,833,293 | B2 | 9/2014 | Horn |
| 8,840,628 | B2 | 9/2014 | Green et al. |
| 8,852,162 | B2 | 10/2014 | Williams et al. |
| 8,852,167 | B2 | 10/2014 | Trombley et al. |
| 8,864,792 | B2 | 10/2014 | Eckhouse et al. |
| 8,876,726 | B2 | 11/2014 | Amit et al. |
| 8,876,854 | B2 | 11/2014 | Christiansen et al. |
| 8,894,610 | B2 | 11/2014 | Macnamara et al. |
| 8,900,257 | B2 | 12/2014 | Straub et al. |
| 8,905,969 | B2 | 12/2014 | Nystrom et al. |
| 8,932,320 | B1 | 1/2015 | Janardhan et al. |
| 8,939,963 | B2 | 1/2015 | Rogers et al. |
| RE45,380 | E | 2/2015 | Root et al. |
| 8,961,491 | B2 | 2/2015 | Uber et al. |
| 8,968,333 | B2 | 3/2015 | Yu et al. |
| 8,968,383 | B1 | 3/2015 | Johnson et al. |
| 8,974,408 | B2 | 3/2015 | Wallace et al. |
| 8,974,411 | B2 | 3/2015 | McKinnon |
| 8,974,420 | B2 | 3/2015 | Searfoss et al. |
| 8,979,871 | B2 | 3/2015 | Tye |
| 8,986,246 | B2 | 3/2015 | Foley et al. |
| 8,992,506 | B2 | 3/2015 | Gulachenski |
| 8,996,095 | B2 | 3/2015 | Anderson et al. |
| 8,998,946 | B2 | 4/2015 | Morero |
| 9,005,237 | B2 | 4/2015 | Eckhouse et al. |
| 9,005,271 | B2 | 4/2015 | Ivancev |
| 9,014,786 | B2 | 4/2015 | Carmeli et al. |
| 9,017,309 | B2 | 4/2015 | Tanikawa et al. |
| 9,023,070 | B2 | 5/2015 | Levine et al. |
| 9,034,008 | B2 | 5/2015 | Eckhouse et al. |
| 9,039,715 | B2 | 5/2015 | Diamant et al. |
| 9,056,200 | B2 | 6/2015 | Uber et al. |
| 9,066,740 | B2 | 6/2015 | Carlson et al. |
| 9,070,486 | B2 | 6/2015 | Guerrera et al. |
| 9,079,000 | B2 | 7/2015 | Hanson et al. |
| 9,095,681 | B2 | 8/2015 | Wenderow et al. |
| 9,101,379 | B2 | 8/2015 | Au et al. |
| 9,107,691 | B2 | 8/2015 | Fojtik |
| 9,111,016 | B2 | 8/2015 | Besson et al. |
| 9,119,625 | B2 | 9/2015 | Bachman et al. |
| 9,119,656 | B2 | 9/2015 | Bose et al. |
| 9,132,949 | B2 | 9/2015 | Bidet et al. |
| 9,138,307 | B2 | 9/2015 | Valaie |
| 9,138,566 | B2 | 9/2015 | Cabiri |
| 9,144,383 | B2 | 9/2015 | Zharov |
| 9,144,662 | B2 | 9/2015 | DiCaprio et al. |
| RE45,760 | E | 10/2015 | Root et al. |
| RE45,776 | E | 10/2015 | Root et al. |
| 9,168,356 | B2 | 10/2015 | Wenderow et al. |
| 9,186,046 | B2 | 11/2015 | Ramamurthy et al. |
| 9,199,033 | B1 | 12/2015 | Cowan et al. |
| 9,199,064 | B2 | 12/2015 | Morero |
| 9,205,227 | B2 | 12/2015 | Cohen et al. |
| 9,211,396 | B2 | 12/2015 | Aboytes |
| 9,220,568 | B2 | 12/2015 | Bromander et al. |
| 9,233,225 | B2 | 1/2016 | Hebert |
| 9,238,124 | B2 | 1/2016 | Grayzel et al. |
| 9,241,699 | B1 | 1/2016 | Kume et al. |
| 9,241,768 | B2 | 1/2016 | Sandhu et al. |
| 9,242,252 | B2 | 1/2016 | Eberle et al. |
| 9,259,215 | B2 | 2/2016 | Chou et al. |
| 9,259,228 | B2 | 2/2016 | Cruise et al. |
| 9,259,526 | B2 | 2/2016 | Barron et al. |
| 9,265,512 | B2 | 2/2016 | Garrison et al. |
| 9,278,201 | B2 | 3/2016 | Rapaport et al. |
| 9,282,992 | B2 | 3/2016 | Levine et al. |
| 9,295,527 | B2 | 3/2016 | Kirschenman et al. |
| 9,295,817 | B2 | 3/2016 | Chang |
| 9,314,268 | B2 | 4/2016 | Cahill |
| 9,314,306 | B2 | 4/2016 | Yu |
| 9,314,307 | B2 | 4/2016 | Richmond et al. |
| 9,314,310 | B2 | 4/2016 | Kirschenman et al. |
| 9,314,311 | B2 | 4/2016 | Wenderow et al. |
| 9,314,594 | B2 | 4/2016 | Kirschenman |
| 9,320,479 | B2 | 4/2016 | Wenderow et al. |
| 9,320,573 | B2 | 4/2016 | Sandhu et al. |
| 9,333,324 | B2 | 5/2016 | Cohen et al. |
| 9,339,282 | B2 | 5/2016 | Green et al. |
| 9,345,508 | B2 | 5/2016 | Hendrick |
| 9,345,856 | B2 | 5/2016 | Witte |
| 9,345,859 | B2 | 5/2016 | Blacker |
| 9,351,993 | B2 | 5/2016 | Cruise et al. |
| 9,370,639 | B2 | 6/2016 | Plassman et al. |
| 9,375,223 | B2 | 6/2016 | Wallace |
| 9,375,729 | B2 | 6/2016 | Eberle et al. |
| 9,381,278 | B2 | 7/2016 | Constant et al. |
| 9,398,946 | B2 | 7/2016 | Valaie |
| 9,399,118 | B2 | 7/2016 | Kume et al. |
| RE46,116 | E | 8/2016 | Root et al. |
| 9,402,977 | B2 | 8/2016 | Wenderow et al. |
| 9,408,669 | B2 | 8/2016 | Kokish et al. |
| 9,408,916 | B2 | 8/2016 | Cruise et al. |
| 9,414,819 | B2 | 8/2016 | Fitz et al. |
| 9,421,328 | B2 | 8/2016 | Brueckner et al. |
| 9,427,515 | B1 | 8/2016 | Nystrom |
| 9,427,562 | B2 | 8/2016 | Blacker |
| 9,439,736 | B2 | 9/2016 | Olson |
| 9,439,791 | B2 | 9/2016 | Vong et al. |
| 9,440,018 | B2 | 9/2016 | Levin et al. |
| 9,446,216 | B2 | 9/2016 | Olesky et al. |
| 9,447,890 | B2 | 9/2016 | Jennings et al. |
| 9,451,884 | B2 | 9/2016 | Palovich et al. |
| 9,451,963 | B2 | 9/2016 | Cruise et al. |
| 9,452,276 | B2 | 9/2016 | Duindam et al. |
| 9,452,277 | B2 | 9/2016 | Blacker |
| 9,463,006 | B2 | 10/2016 | Forde et al. |
| 9,474,857 | B2 | 10/2016 | Riley et al. |
| 9,480,797 | B1 | 11/2016 | Swantner et al. |
| 9,480,813 | B2 | 11/2016 | Fukuoka et al. |
| 9,486,221 | B2 | 11/2016 | Cruise et al. |
| 9,488,971 | B2 | 11/2016 | Yip et al. |
| 9,492,637 | B2 | 11/2016 | Garrison et al. |
| 9,498,291 | B2 | 11/2016 | Gilbert et al. |
| 9,504,476 | B2 | 11/2016 | Gulachenski |
| 9,510,855 | B2 | 12/2016 | Rapaport et al. |
| 9,510,912 | B2 | 12/2016 | Bencteux et al. |
| 9,517,305 | B2 | 12/2016 | Uram et al. |
| 9,526,504 | B2 | 12/2016 | Chang |
| 9,526,505 | B2 | 12/2016 | Marks et al. |
| 9,532,792 | B2 | 1/2017 | Galdonik et al. |
| 9,532,840 | B2 | 1/2017 | Wong et al. |
| 9,533,121 | B2 | 1/2017 | Pacheco et al. |
| 9,533,344 | B2 | 1/2017 | Monetti et al. |
| 9,539,022 | B2 | 1/2017 | Bowman |
| 9,539,122 | B2 | 1/2017 | Burke et al. |
| 9,545,497 | B2 | 1/2017 | Wenderow et al. |
| 9,546,236 | B2 | 1/2017 | Cruise et al. |
| 9,549,783 | B2 | 1/2017 | Zirps |
| 9,561,121 | B2 | 2/2017 | Sudin et al. |
| 9,561,125 | B2 | 2/2017 | Bowman et al. |
| 9,561,345 | B2 | 2/2017 | Garrison et al. |
| 9,566,201 | B2 | 2/2017 | Yu |
| 9,566,414 | B2 | 2/2017 | Wong et al. |
| 9,572,481 | B2 | 2/2017 | Duindam et al. |
| 9,585,806 | B2 | 3/2017 | Herrig |
| 9,586,029 | B2 | 3/2017 | Shekalim et al. |
| 9,597,101 | B2 | 3/2017 | Galdonik et al. |
| 9,597,212 | B2 | 3/2017 | Thompson et al. |
| 9,603,573 | B2 | 3/2017 | Leininger et al. |
| 9,615,832 | B2 | 4/2017 | Bose et al. |

(56)                    References Cited

U.S. PATENT DOCUMENTS

| | | | |
|---|---|---|---|
| 9,622,753 B2 | 4/2017 | Cox |
| 9,623,209 B2 | 4/2017 | Wenderow et al. |
| 9,623,228 B2 | 4/2017 | Ryan et al. |
| 9,629,595 B2 | 4/2017 | Walker et al. |
| 9,636,479 B2 | 5/2017 | Bencteux et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,687,304 B2 | 6/2017 | Bencteux et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,700,698 B2 | 7/2017 | Pacheco et al. |
| 9,707,377 B2 | 7/2017 | Cohen et al. |
| 9,707,380 B2 | 7/2017 | Qiu et al. |
| 9,717,500 B2 | 8/2017 | Tieu et al. |
| 9,724,103 B2 | 8/2017 | Cruise et al. |
| 9,724,491 B2 | 8/2017 | Solar et al. |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,111 B2 | 9/2017 | Gulachenski |
| 9,764,114 B2 | 9/2017 | Murphy et al. |
| 9,770,251 B2 | 9/2017 | Bowman et al. |
| 9,770,301 B2 | 9/2017 | Bencteux et al. |
| 9,775,730 B1 | 10/2017 | Waltzman |
| 9,782,130 B2 | 10/2017 | Hauck et al. |
| 9,782,564 B2 | 10/2017 | Zirps et al. |
| 9,789,242 B2 | 10/2017 | Criado et al. |
| 9,789,283 B2 | 10/2017 | Richter et al. |
| 9,789,285 B1 | 10/2017 | Blacker |
| 9,801,643 B2 | 10/2017 | Hansen et al. |
| 9,803,043 B2 | 10/2017 | Cruise et al. |
| 9,808,610 B2 | 11/2017 | Li et al. |
| 9,814,534 B2 | 11/2017 | Wenderow et al. |
| 9,820,761 B2 | 11/2017 | Garrison et al. |
| 9,825,455 B2 | 11/2017 | Sandhu et al. |
| 9,827,047 B2 | 11/2017 | Fudaba et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,072 B2 | 1/2018 | Moberg et al. |
| 9,855,101 B2 | 1/2018 | Wenderow et al. |
| 9,861,783 B2 | 1/2018 | Garrison et al. |
| 9,877,731 B2 | 1/2018 | Cruise et al. |
| 9,877,742 B2 | 1/2018 | Milner et al. |
| 9,883,885 B2 | 2/2018 | Hendrick et al. |
| 9,907,880 B2 | 3/2018 | Cruise et al. |
| 9,913,960 B2 | 3/2018 | Blanchard et al. |
| 9,931,129 B2 | 4/2018 | Walish et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,987,027 B2 | 6/2018 | Ben-Ami |
| 9,987,028 B2 | 6/2018 | Lowinger et al. |
| 9,993,614 B2 | 6/2018 | Pacheco et al. |
| 9,993,615 B2 | 6/2018 | Blacker |
| 9,999,355 B2 | 6/2018 | Kirenko |
| 9,999,751 B2 | 6/2018 | Pacheco et al. |
| 10,010,698 B2 | 7/2018 | Watanabe et al. |
| 10,010,699 B2 | 7/2018 | Cohen et al. |
| 10,028,854 B2 | 7/2018 | Tatalovich et al. |
| 10,029,072 B2 | 7/2018 | Hebert |
| 10,039,906 B2 | 8/2018 | Kume et al. |
| 10,046,140 B2 | 8/2018 | Kokish et al. |
| 10,052,761 B2 | 8/2018 | Langenfeld et al. |
| 10,070,878 B2 | 9/2018 | Ma |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,086,169 B2 | 10/2018 | Grayzel et al. |
| 10,105,154 B1 | 10/2018 | Green |
| 10,105,486 B2 | 10/2018 | Trombley et al. |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,178,995 B2 | 1/2019 | Cragg |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,201,314 B2 | 2/2019 | Frederick et al. |
| 10,207,077 B2 | 2/2019 | Griggin et al. |
| 10,213,582 B2 | 2/2019 | Garrison et al. |
| 10,226,277 B2 | 3/2019 | Smith et al. |
| 10,231,788 B2 | 3/2019 | Olson et al. |
| 10,238,456 B2 | 3/2019 | Murphy et al. |
| 10,238,833 B2 | 3/2019 | Christian et al. |
| 10,245,112 B2 | 4/2019 | Kottenstette et al. |
| 10,258,285 B2 | 4/2019 | Hauck et al. |
| 10,258,452 B2 | 4/2019 | Eckhouse et al. |
| 10,265,086 B2 | 4/2019 | Vale |
| 10,271,864 B2 | 4/2019 | Greenhalgh et al. |
| 10,271,910 B2 | 4/2019 | Wenderow et al. |
| RE47,376 E | 5/2019 | Pokorney et al. |
| 10,278,678 B2 | 5/2019 | Peliks |
| 10,278,816 B2 | 5/2019 | Miller |
| 10,299,867 B2 | 5/2019 | Wenderow et al. |
| 10,300,256 B2 | 5/2019 | Aboytes |
| 10,307,570 B2 | 6/2019 | Blacker |
| 10,322,277 B2 | 6/2019 | Nystrom |
| 10,327,790 B2 | 6/2019 | Garrison et al. |
| 10,335,186 B2 | 7/2019 | Rosenbluth et al. |
| 10,342,570 B2 | 7/2019 | Richter et al. |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,383,691 B2 | 8/2019 | Hendrick et al. |
| 10,383,751 B2 | 8/2019 | Ferrera et al. |
| 10,384,034 B2 | 8/2019 | Garrison et al. |
| 10,391,234 B2 | 8/2019 | Sams et al. |
| 10,420,537 B2 | 9/2019 | Salahieh et al. |
| 10,420,581 B2 | 9/2019 | Hehrlein |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,441,745 B2 | 10/2019 | Yang et al. |
| 10,449,007 B2 | 10/2019 | Deboeuf et al. |
| 10,456,552 B2 | 10/2019 | Goyal |
| 10,456,556 B2 | 10/2019 | Cabiri |
| 10,471,233 B2 | 11/2019 | Garrison et al. |
| 10,512,514 B2 | 12/2019 | Nowlin et al. |
| 10,522,250 B2 | 12/2019 | Spohn et al. |
| 10,524,814 B2 | 1/2020 | Chang et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,537,706 B2 | 1/2020 | Kanemasa et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,569,049 B2 | 2/2020 | Garrison et al. |
| 10,583,276 B2 | 3/2020 | Zirps |
| 10,588,656 B2 | 3/2020 | Trosper et al. |
| 10,589,018 B2 | 3/2020 | Uber et al. |

(56) References Cited

U.S. PATENT DOCUMENTS

| | | | |
|---|---|---|---|
| D881,234 S | 4/2020 | Capela |
| 10,610,256 B2 | 4/2020 | Bowman |
| 10,610,668 B2 | 4/2020 | Burkholz et al. |
| 10,611,391 B1 | 4/2020 | Klem et al. |
| 10,646,239 B2 | 5/2020 | Garrison et al. |
| 10,647,007 B2 | 5/2020 | Cordoba et al. |
| 10,653,426 B2 | 5/2020 | Yang et al. |
| 10,653,434 B1 | 5/2020 | Yang et al. |
| 10,653,863 B1 | 5/2020 | Blacker et al. |
| 10,660,814 B2 | 5/2020 | Soundararajan et al. |
| 10,661,053 B2 | 5/2020 | Yang et al. |
| 10,661,453 B2 | 5/2020 | Koenig et al. |
| 10,668,192 B2 | 6/2020 | Raney et al. |
| 10,687,903 B2 | 6/2020 | Lewis et al. |
| 10,695,140 B2 | 6/2020 | Overmyer et al. |
| 10,695,159 B2 | 6/2020 | Hauser |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |
| 10,716,880 B2 | 7/2020 | Culbert et al. |
| 10,716,915 B2 | 7/2020 | Ogle et al. |
| 10,722,251 B2 | 7/2020 | Garrison et al. |
| 10,722,253 B2 | 7/2020 | Deville et al. |
| 10,722,683 B2 | 7/2020 | Solar et al. |
| 10,729,825 B2 | 8/2020 | Boyle, Jr. et al. |
| 10,736,706 B2 | 8/2020 | Scheib |
| 10,737,061 B2 | 8/2020 | Parmar |
| 10,743,893 B2 | 8/2020 | Garrison et al. |
| 10,744,302 B2 | 8/2020 | Pacheco et al. |
| 10,751,073 B2 | 8/2020 | Eckhouse et al. |
| 10,765,303 B2 | 9/2020 | Graetzel et al. |
| 10,765,486 B2 | 9/2020 | Bajo et al. |
| 10,772,647 B2 | 9/2020 | Ben-Ami |
| 10,779,775 B2 | 9/2020 | Bergman et al. |
| 10,779,895 B2 | 9/2020 | Wenderow et al. |
| 10,783,993 B2 | 9/2020 | Spohn et al. |
| 10,786,268 B2 | 9/2020 | Ben-Ami |
| 10,786,270 B2 | 9/2020 | Yang et al. |
| 10,792,056 B2 | 10/2020 | Vale et al. |
| 10,799,305 B2 | 10/2020 | Murphy et al. |
| 10,806,905 B2 | 10/2020 | Asmus |
| 10,813,713 B2 | 10/2020 | Koch et al. |
| 10,814,102 B2 | 10/2020 | Laby et al. |
| 10,820,951 B2 | 11/2020 | Soundararajan et al. |
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafii-Tari et al. |
| 10,835,272 B2 | 11/2020 | Yang et al. |
| 10,835,278 B2 | 11/2020 | Wilke et al. |
| 10,835,329 B2 | 11/2020 | Wenderow et al. |
| 10,835,668 B2 | 11/2020 | Novickoff et al. |
| 10,835,711 B2 | 11/2020 | Yang et al. |
| 10,849,702 B2 | 12/2020 | Hsu et al. |
| 10,856,898 B2 | 12/2020 | Matsushita et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,888,280 B2 | 1/2021 | Newberry |
| 10,898,082 B2 | 1/2021 | Sandgaard |
| 10,898,288 B2 | 1/2021 | Dachs, II et al. |
| 10,900,771 B2 | 1/2021 | Kottenstette et al. |
| 10,905,850 B2 | 2/2021 | Christian et al. |
| 10,912,624 B2 | 2/2021 | Prentakis et al. |
| 10,912,924 B2 | 2/2021 | Park et al. |
| 10,945,904 B2 | 3/2021 | de Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,020,030 B2 | 6/2021 | Tao et al. |
| 11,020,059 B2 | 6/2021 | Sheth et al. |
| 11,040,147 B2 | 6/2021 | Wagner |
| 11,045,274 B2 | 6/2021 | Dachs, II et al. |
| 11,052,226 B2 | 7/2021 | Salahieh et al. |
| 11,058,508 B2 | 7/2021 | Scheib et al. |
| 11,065,018 B2 | 7/2021 | Buck et al. |
| 11,076,876 B2 | 8/2021 | Vale |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |
| 11,096,712 B2 | 8/2021 | Teigen et al. |
| 11,104,012 B2 | 8/2021 | Cordoba et al. |
| 11,109,919 B2 | 9/2021 | Murphy et al. |
| 11,109,920 B2 | 9/2021 | Al-Jadda et al. |
| 11,109,921 B2 | 9/2021 | Kottenstette et al. |
| 11,110,217 B2 | 9/2021 | O'Brien et al. |
| 11,114,918 B2 | 9/2021 | Zirps |
| 11,123,090 B2 | 9/2021 | Yang et al. |
| 11,129,602 B2 | 9/2021 | Wong et al. |
| 11,134,859 B2 | 10/2021 | Strasser |
| 11,141,566 B2 | 10/2021 | Cabiri |
| 11,147,949 B2 | 10/2021 | Yang et al. |
| 11,147,950 B2 | 10/2021 | Destrebecq et al. |
| 11,179,213 B2 | 11/2021 | Huang et al. |
| 11,179,546 B2 | 11/2021 | Martin |
| 11,185,455 B2 | 11/2021 | Cagle et al. |
| 11,191,893 B2 | 12/2021 | Capone et al. |
| 11,197,683 B1 | 12/2021 | Teigen et al. |
| 11,197,771 B2 | 12/2021 | Ferrera et al. |
| 11,207,096 B2 | 12/2021 | To et al. |
| 11,207,147 B2 | 12/2021 | Diamond et al. |
| 11,207,497 B1 | 12/2021 | Yee et al. |
| 11,209,300 B2 | 12/2021 | Johnson |
| 11,213,356 B2 | 1/2022 | Tanner et al. |
| 11,213,362 B2 | 1/2022 | Sharon et al. |
| 11,213,654 B2 | 1/2022 | Murphy et al. |
| 11,224,457 B2 | 1/2022 | Brinkmann et al. |
| 11,234,779 B2 | 2/2022 | Fuerst et al. |
| 11,234,781 B2 | 2/2022 | Penny et al. |
| 11,234,784 B2 | 2/2022 | Alden |
| 11,241,291 B2 | 2/2022 | Sharon et al. |
| 11,253,292 B2 | 2/2022 | McGuckin, Jr. et al. |
| 11,259,881 B2 | 3/2022 | Garcia Kilroy et al. |
| 11,266,424 B2 | 3/2022 | Hofmann et al. |
| 11,291,515 B2 | 4/2022 | Sharon et al. |
| 11,298,198 B2 | 4/2022 | Fournier et al. |
| 11,304,668 B2 | 4/2022 | Wenderow et al. |
| 11,318,618 B2 | 5/2022 | Desai |
| 11,331,157 B2 | 5/2022 | Russell et al. |
| 11,337,712 B2 | 5/2022 | Teigen et al. |
| 11,337,764 B2 | 5/2022 | Deboeuf et al. |
| 11,357,586 B2 | 6/2022 | Huang et al. |
| 11,357,597 B2 | 6/2022 | Jhaveri et al. |
| 11,359,156 B2 | 6/2022 | Long et al. |
| 11,376,086 B2 | 7/2022 | McGrogan et al. |
| 11,389,360 B2 | 7/2022 | Koenig et al. |
| 11,400,214 B2 | 8/2022 | Porter |
| 11,406,402 B2 | 8/2022 | Deville et al. |
| 11,413,101 B2 | 8/2022 | Sen et al. |
| 11,413,431 B2 | 8/2022 | Blacker |
| 11,419,977 B2 | 8/2022 | Cowan et al. |
| 11,426,246 B2 | 8/2022 | Asadian et al. |
| 11,432,835 B2 | 9/2022 | Shaffer et al. |
| 11,432,840 B2 | 9/2022 | Grothe et al. |
| 11,448,327 B2 | 9/2022 | Heffner et al. |
| 11,464,587 B2 | 10/2022 | Yu et al. |
| 11,472,030 B2 | 10/2022 | Ho et al. |
| 11,478,329 B2 | 10/2022 | Gee et al. |
| 11,490,911 B2 | 11/2022 | Panian |
| 11,497,481 B2 | 11/2022 | Penny et al. |
| 11,497,523 B2 | 11/2022 | Trosper et al. |
| 11,497,568 B2 | 11/2022 | Ho et al. |
| 11,510,736 B2 | 11/2022 | Rafii-Tari et al. |

(56) References Cited

U.S. PATENT DOCUMENTS

| | | | |
|---|---|---|---|
| D976,399 | S | 1/2023 | Carmi |
| 11,547,426 | B2 | 1/2023 | Deville et al. |
| 11,547,511 | B2 | 1/2023 | Asadian et al. |
| 11,564,649 | B2 | 1/2023 | Kedmi-Shahar et al. |
| 11,571,267 | B2 | 2/2023 | Gonenc et al. |
| 11,576,743 | B2 | 2/2023 | Venkataraman et al. |
| 11,577,382 | B2 | 2/2023 | Cagle et al. |
| 11,589,931 | B2 | 2/2023 | Desai et al. |
| 11,607,108 | B2 | 3/2023 | Yu et al. |
| 11,628,024 | B2 | 4/2023 | Kapadia |
| 11,633,247 | B2 | 4/2023 | Johnson et al. |
| 11,642,181 | B2 | 5/2023 | Nobles et al. |
| 11,653,905 | B2 | 5/2023 | Wong et al. |
| 11,660,151 | B2 | 5/2023 | Schena |
| 11,660,437 | B2 | 5/2023 | Verma |
| 11,672,602 | B2 | 6/2023 | Monteverde et al. |
| 11,678,943 | B2 | 6/2023 | Zhou et al. |
| 11,678,948 | B2 | 6/2023 | Vargas et al. |
| 11,684,759 | B2 | 6/2023 | Hayzelden |
| 11,690,985 | B2 | 7/2023 | Calhoun et al. |
| 11,696,808 | B2 | 7/2023 | Blacker et al. |
| 11,696,810 | B2 | 7/2023 | Asadian et al. |
| 11,701,196 | B2 | 7/2023 | Scheib et al. |
| 11,703,604 | B2 | 7/2023 | Dissertori et al. |
| 11,712,805 | B2 | 8/2023 | Zhou et al. |
| 11,713,376 | B2 | 8/2023 | Leroux et al. |
| 11,717,356 | B2 | 8/2023 | Amiri et al. |
| 11,717,640 | B2 | 8/2023 | Fantuzzi et al. |
| 11,723,739 | B2 | 8/2023 | Asadian et al. |
| 11,723,744 | B2 | 8/2023 | Ergueta Tejerina et al. |
| 11,737,821 | B2 | 8/2023 | Algawi et al. |
| 11,744,989 | B2 | 9/2023 | Blacker |
| 11,759,269 | B2 | 9/2023 | Zhou et al. |
| 11,764,873 | B2 | 9/2023 | Burla et al. |
| 11,766,786 | B2 | 9/2023 | Cordoba et al. |
| 11,780,092 | B2 | 10/2023 | Desai et al. |
| 11,785,938 | B2 | 10/2023 | Clavien et al. |
| 11,786,329 | B2 | 10/2023 | Fuerst et al. |
| 11,793,500 | B2 | 10/2023 | Vargas |
| 11,793,597 | B2 | 10/2023 | Vargas et al. |
| 11,801,365 | B2 | 10/2023 | Blacker et al. |
| 11,813,203 | B2 | 11/2023 | Timm et al. |
| 11,819,295 | B2 | 11/2023 | Wenderow et al. |
| 11,832,904 | B2 | 12/2023 | Wenderow et al. |
| 11,844,580 | B2 | 12/2023 | Sen et al. |
| 11,844,732 | B2 | 12/2023 | Klem et al. |
| 11,883,119 | B2 | 1/2024 | Sen et al. |
| 11,883,245 | B2 | 1/2024 | Fathollahi Ghezelghieh et al. |
| 11,890,024 | B2 | 2/2024 | Panian |
| 11,890,432 | B2 | 2/2024 | Awad et al. |
| 11,896,325 | B2 | 2/2024 | Clark et al. |
| 11,903,669 | B2 | 2/2024 | Cope et al. |
| 11,906,009 | B2 | 2/2024 | Klem |
| 11,911,120 | B2 | 2/2024 | Freiin von Kapri et al. |
| 11,911,910 | B2 | 2/2024 | Gonenc et al. |
| 11,918,240 | B2 | 3/2024 | Deville et al. |
| 11,918,312 | B2 | 3/2024 | Yu |
| 11,918,423 | B2 | 3/2024 | Kottenstette et al. |
| 11,998,290 | B2 | 6/2024 | Murphy et al. |
| 12,004,829 | B2 | 6/2024 | Searfoss et al. |
| 12,005,589 | B2 | 6/2024 | Rea et al. |
| 12,035,989 | B2 | 7/2024 | Clark et al. |
| 12,046,363 | B2 | 7/2024 | Shrivastava et al. |
| 12,059,161 | B2 | 8/2024 | Deville et al. |
| 12,059,225 | B2 | 8/2024 | Zhou et al. |
| 12,076,036 | B2 | 9/2024 | Baron et al. |
| 12,076,099 | B2 | 9/2024 | Shrivastava et al. |
| 12,076,497 | B2 | 9/2024 | Fantuzzi et al. |
| 12,076,505 | B2 | 9/2024 | Haubert |
| 12,082,982 | B2 | 9/2024 | Jhaveri et al. |
| 12,087,024 | B2 | 9/2024 | Djelouah et al. |
| 12,102,290 | B2 | 10/2024 | Sharon et al. |
| 12,114,940 | B2 | 10/2024 | Garcia Kilroy et al. |
| 12,117,624 | B2 | 10/2024 | Fuerst et al. |
| 12,133,631 | B2 | 11/2024 | Saadat et al. |
| 12,133,700 | B2 | 11/2024 | Miller et al. |
| 12,133,702 | B2 | 11/2024 | Nowlin et al. |
| 12,133,704 | B2 | 11/2024 | Savall et al. |
| 12,133,707 | B2 | 11/2024 | Zhang et al. |
| 12,133,965 | B2 | 11/2024 | Chassot et al. |
| 12,136,867 | B2 | 11/2024 | Zirps |
| 12,137,603 | B2 | 11/2024 | Liu et al. |
| 12,137,874 | B2 | 11/2024 | Deyanov et al. |
| 12,137,880 | B2 | 11/2024 | Retailleau et al. |
| 12,137,926 | B2 | 11/2024 | Cooper |
| 12,137,935 | B2 | 11/2024 | Blumenkranz et al. |
| 12,137,936 | B2 | 11/2024 | Litke et al. |
| 12,137,990 | B2 | 11/2024 | Walker et al. |
| 12,138,002 | B2 | 11/2024 | Fenech |
| 12,138,003 | B2 | 11/2024 | Schuh |
| 12,138,004 | B2 | 11/2024 | Cone et al. |
| 12,138,006 | B2 | 11/2024 | Ramstad et al. |
| 12,138,012 | B2 | 11/2024 | Barbagli et al. |
| 12,138,129 | B2 | 11/2024 | Yuan et al. |
| 12,138,130 | B2 | 11/2024 | Garbus et al. |
| 12,140,172 | B2 | 11/2024 | Grout et al. |
| 12,144,564 | B2 | 11/2024 | Barbagli et al. |
| 12,144,569 | B2 | 11/2024 | Cone et al. |
| 12,144,574 | B2 | 11/2024 | Griffiths et al. |
| 12,144,575 | B2 | 11/2024 | Torabi |
| 12,144,690 | B2 | 11/2024 | Fuerst et al. |
| 12,145,278 | B2 | 11/2024 | Ho et al. |
| 12,148,320 | B2 | 11/2024 | Alexander et al. |
| 12,150,645 | B2 | 11/2024 | Meade et al. |
| 12,150,660 | B1 | 11/2024 | Teigen et al. |
| 12,150,692 | B2 | 11/2024 | Shah et al. |
| 12,150,718 | B2 | 11/2024 | Barbagli et al. |
| 12,150,723 | B2 | 11/2024 | Ayvali et al. |
| 12,150,796 | B2 | 11/2024 | Wenderow et al. |
| 12,150,819 | B2 | 11/2024 | Hazelton et al. |
| 12,156,654 | B2 | 12/2024 | Wellman |
| 12,156,666 | B2 | 12/2024 | Trosper et al. |
| 12,156,667 | B2 | 12/2024 | Trosper et al. |
| 12,156,711 | B2 | 12/2024 | Liao et al. |
| 12,156,755 | B2 | 12/2024 | Walker et al. |
| 12,157,238 | B2 | 12/2024 | Fredrickson et al. |
| 12,161,286 | B2 | 12/2024 | Hazelton et al. |
| 12,161,290 | B2 | 12/2024 | Liou et al. |
| 12,161,306 | B2 | 12/2024 | Blumenkranz et al. |
| 12,161,321 | B2 | 12/2024 | Weir et al. |
| 12,161,419 | B2 | 12/2024 | Fuerst et al. |
| 12,161,423 | B2 | 12/2024 | Chopra et al. |
| 12,161,434 | B2 | 12/2024 | Panescu et al. |
| 12,161,435 | B2 | 12/2024 | Abbott et al. |
| 12,161,512 | B2 | 12/2024 | Shirazian et al. |
| 12,161,822 | B2 | 12/2024 | Kim et al. |
| 12,162,143 | B2 | 12/2024 | Dimaio et al. |
| 12,164,684 | B2 | 12/2024 | Itkowitz et al. |
| 12,165,268 | B2 | 12/2024 | Olson et al. |
| 12,165,317 | B2 | 12/2024 | Proksch et al. |
| 12,167,943 | B2 | 12/2024 | Azizian et al. |
| 12,171,398 | B2 | 12/2024 | Halderman et al. |
| 12,171,401 | B2 | 12/2024 | Brichard et al. |
| 12,171,435 | B2 | 12/2024 | Kaufman et al. |
| 12,171,504 | B2 | 12/2024 | Rafii-Tari |
| 12,171,505 | B2 | 12/2024 | Barbagli et al. |
| 12,171,511 | B2 | 12/2024 | Gonenc et al. |
| 12,171,514 | B2 | 12/2024 | Soundararajan et al. |
| 12,171,516 | B2 | 12/2024 | Abbott et al. |
| 12,171,543 | B2 | 12/2024 | Duindam et al. |
| 12,171,955 | B2 | 12/2024 | Wenderow et al. |
| 12,171,958 | B2 | 12/2024 | Kim et al. |
| 12,175,018 | B2 | 12/2024 | Freiin von Kapri et al. |
| 12,177,411 | B2 | 12/2024 | Culman |
| 12,178,387 | B2 | 12/2024 | McDowall et al. |
| 12,178,399 | B2 | 12/2024 | Itkowitz et al. |
| 12,178,431 | B2 | 12/2024 | Ueda et al. |
| 12,178,521 | B2 | 12/2024 | Sramek et al. |
| 12,178,526 | B2 | 12/2024 | McKenney et al. |
| 12,178,534 | B2 | 12/2024 | Asadian et al. |
| 12,182,956 | B2 | 12/2024 | Harris, Jr. |
| 12,185,947 | B2 | 1/2025 | Hart |
| 12,191,031 | B2 | 1/2025 | Azizian et al. |
| 12,201,484 | B2 | 1/2025 | Itkowitz et al. |

(56)                    References Cited

U.S. PATENT DOCUMENTS

| | | |
|---|---|---|
| 12,201,485 B2 | 1/2025 | McDowall et al. |
| 12,212,240 B2 | 1/2025 | Schulz |
| 2001/0031980 A1 | 10/2001 | Wensel et al. |
| 2001/0031981 A1 | 10/2001 | Evans et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg et al. |
| 2002/0113501 A1 | 8/2002 | Doi |
| 2002/0156459 A1 | 10/2002 | Ye et al. |
| 2002/0156460 A1 | 10/2002 | Ye et al. |
| 2002/0169467 A1 | 11/2002 | Heitzmann et al. |
| 2002/0173812 A1 | 11/2002 | McGuckin et al. |
| 2002/0177899 A1 | 11/2002 | Eum et al. |
| 2002/0188314 A1 | 12/2002 | Anderson et al. |
| 2002/0192113 A1 | 12/2002 | Uffenheimer et al. |
| 2003/0071285 A1 | 4/2003 | Tsukernik |
| 2003/0088266 A1 | 5/2003 | Bowlin |
| 2003/0100849 A1 | 5/2003 | Jang |
| 2003/0105451 A1 | 6/2003 | Westlund et al. |
| 2003/0114739 A1* | 6/2003 | Fuimaono ............... A61B 5/061 |
| | | 600/374 |
| 2003/0125673 A1 | 7/2003 | Houde et al. |
| 2003/0135193 A1 | 7/2003 | Hilgers et al. |
| 2003/0135198 A1 | 7/2003 | Berhow et al. |
| 2003/0153847 A1 | 8/2003 | Sandler et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0068248 A1 | 4/2004 | Mooney et al. |
| 2004/0097805 A1 | 5/2004 | Verard et al. |
| 2004/0138693 A1 | 7/2004 | Eskuri et al. |
| 2004/0143225 A1 | 7/2004 | Callan |
| 2004/0153049 A1 | 8/2004 | Hewitt et al. |
| 2004/0199201 A1 | 10/2004 | Kellett et al. |
| 2004/0215222 A1 | 10/2004 | Krivoruchko |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1 | 1/2005 | Deckman et al. |
| 2005/0055047 A1 | 3/2005 | Greenhalgh |
| 2005/0059957 A1 | 3/2005 | Campbell et al. |
| 2005/0077225 A1 | 4/2005 | Usher et al. |
| 2005/0080400 A1 | 4/2005 | Corcoran et al. |
| 2005/0103332 A1 | 5/2005 | Gingles et al. |
| 2005/0107667 A1 | 5/2005 | Danitz |
| 2005/0124985 A1 | 6/2005 | Takayama et al. |
| 2005/0137680 A1 | 6/2005 | Ortiz et al. |
| 2005/0165276 A1 | 7/2005 | Belson et al. |
| 2005/0182386 A1 | 8/2005 | Aggerholm |
| 2005/0187570 A1 | 8/2005 | Nguyen et al. |
| 2005/0228417 A1 | 10/2005 | Teitelbaum |
| 2005/0277912 A1 | 12/2005 | John |
| 2006/0011501 A1 | 1/2006 | Itou et al. |
| 2006/0020285 A1 | 1/2006 | Niermann |
| 2006/0020286 A1 | 1/2006 | Niermann |
| 2006/0030835 A1 | 2/2006 | Sherman et al. |
| 2006/0064036 A1 | 3/2006 | Osborne et al. |
| 2006/0074401 A1 | 4/2006 | Ross |
| 2006/0089618 A1 | 4/2006 | McFerran et al. |
| 2006/0095022 A1 | 5/2006 | Moll et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0200026 A1 | 9/2006 | Wallace et al. |
| 2006/0200191 A1 | 9/2006 | Zadno-Azizi |
| 2006/0217664 A1 | 9/2006 | Hattler et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0038225 A1 | 2/2007 | Osborne et al. |
| 2007/0043333 A1 | 2/2007 | Kampa et al. |
| 2007/0060888 A1 | 3/2007 | Goff et al. |
| 2007/0060915 A1 | 3/2007 | Kucklick |
| 2007/0106208 A1 | 5/2007 | Uber et al. |
| 2007/0142824 A1 | 6/2007 | Devengenzo |
| 2007/0179473 A1 | 8/2007 | Masters et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2007/0239182 A1 | 10/2007 | Glines et al. |
| 2007/0270639 A1 | 11/2007 | Long |
| 2008/0027464 A1 | 1/2008 | Moll et al. |
| 2008/0045881 A1 | 2/2008 | Teitelbaum et al. |
| 2008/0064984 A1 | 3/2008 | Pflueger et al. |
| 2008/0086051 A1 | 4/2008 | Voegele |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234631 A1 | 9/2008 | Reis |
| 2008/0234715 A1 | 9/2008 | Pesce |
| 2008/0262350 A1 | 10/2008 | Unger |
| 2008/0262513 A1 | 10/2008 | Stahler et al. |
| 2008/0294058 A1 | 11/2008 | Shklarski |
| 2008/0300544 A1 | 12/2008 | Palm et al. |
| 2008/0312639 A1 | 12/2008 | Weber |
| 2008/0319387 A1 | 12/2008 | Amisar et al. |
| 2009/0030400 A1 | 1/2009 | Bose et al. |
| 2009/0043330 A1 | 2/2009 | To |
| 2009/0076445 A1 | 3/2009 | Furnish |
| 2009/0093829 A1 | 4/2009 | Melsheimer et al. |
| 2009/0131955 A1 | 5/2009 | Wenderow et al. |
| 2009/0138031 A1 | 5/2009 | Tsukernik |
| 2009/0153374 A1 | 6/2009 | Maw et al. |
| 2009/0171332 A1 | 7/2009 | Bonneau |
| 2009/0171368 A1 | 7/2009 | Pearce et al. |
| 2009/0182370 A1 | 7/2009 | Volobuyev et al. |
| 2009/0187143 A1 | 7/2009 | Vreeman |
| 2009/0204078 A1 | 8/2009 | Mitchell et al. |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0254083 A1 | 10/2009 | Wallace et al. |
| 2009/0264785 A1 | 10/2009 | Causevic et al. |
| 2009/0264865 A1 | 10/2009 | Kawai |
| 2009/0270800 A1 | 10/2009 | Spurchise et al. |
| 2009/0270888 A1 | 10/2009 | Patel et al. |
| 2009/0275974 A1 | 11/2009 | Marchand et al. |
| 2009/0287190 A1 | 11/2009 | Shippert |
| 2009/0312699 A1 | 12/2009 | Pudelko |
| 2010/0023033 A1 | 1/2010 | Mauch et al. |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0069833 A1* | 3/2010 | Wenderow ....... A61B 17/00234 |
| | | 604/95.01 |
| 2010/0114017 A1 | 5/2010 | Lenker et al. |
| 2010/0114022 A1 | 5/2010 | Hirszowicz et al. |
| 2010/0125253 A1 | 5/2010 | Olson et al. |
| 2010/0137793 A1 | 6/2010 | Hirszowicz et al. |
| 2010/0175701 A1* | 7/2010 | Reis ........................ A61B 34/30 |
| | | 74/461 |
| 2010/0204712 A1* | 8/2010 | Mallaby ................. A61B 17/22 |
| | | 606/128 |
| 2010/0204713 A1 | 8/2010 | Ruiz Morales |
| 2010/0217235 A1 | 8/2010 | Thorstenson et al. |
| 2010/0217276 A1 | 8/2010 | Garrison et al. |
| 2010/0280363 A1 | 11/2010 | Skarda et al. |
| 2010/0286756 A1 | 11/2010 | Dorn |
| 2010/0312141 A1 | 12/2010 | Keast et al. |
| 2010/0331916 A1 | 12/2010 | Parramon et al. |
| 2011/0004223 A1 | 1/2011 | Leeflang |
| 2011/0009875 A1 | 1/2011 | Grandfield et al. |
| 2011/0015484 A1 | 1/2011 | Alvarez et al. |
| 2011/0034986 A1 | 2/2011 | Chou |
| 2011/0054504 A1 | 3/2011 | Porter |

(56) References Cited

U.S. PATENT DOCUMENTS

| | | |
|---|---|---|
| 2011/0077620 A1 | 3/2011 | deBeer |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0144658 A1 | 6/2011 | Wenderow et al. |
| 2011/0152920 A1 | 6/2011 | Eckhouse et al. |
| 2011/0152998 A1 | 6/2011 | Berez et al. |
| 2011/0166447 A1 | 7/2011 | Windolf |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0238010 A1 | 9/2011 | Kirschenman et al. |
| 2011/0238041 A1 | 9/2011 | Lim et al. |
| 2011/0288544 A1 | 11/2011 | Verin et al. |
| 2011/0295217 A1 | 12/2011 | Tanaka et al. |
| 2011/0313318 A1 | 12/2011 | Rule et al. |
| 2012/0016407 A1 | 1/2012 | Sakai |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0071895 A1 | 3/2012 | Stahler et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0143237 A1 | 6/2012 | Cam et al. |
| 2012/0150147 A1 | 6/2012 | Leynov et al. |
| 2012/0172798 A1 | 7/2012 | Miller et al. |
| 2012/0179032 A1 | 7/2012 | Bromander et al. |
| 2012/0259718 A1 | 10/2012 | Miller et al. |
| 2012/0290067 A1 | 11/2012 | Cam et al. |
| 2012/0296362 A1 | 11/2012 | Cam et al. |
| 2012/0316458 A1 | 12/2012 | Rahman et al. |
| 2012/0330196 A1 | 12/2012 | Nita |
| 2013/0006225 A1 | 1/2013 | Cucin |
| 2013/0012924 A1 | 1/2013 | Davis et al. |
| 2013/0018318 A1 | 1/2013 | Ravichandran et al. |
| 2013/0018359 A1 | 1/2013 | Coyle |
| 2013/0030408 A1 | 1/2013 | Piferi |
| 2013/0030461 A1 | 1/2013 | Marks et al. |
| 2013/0035537 A1 | 2/2013 | Wallace |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0053704 A1 | 2/2013 | Bernak et al. |
| 2013/0096551 A1 | 4/2013 | Govari et al. |
| 2013/0116701 A1 | 5/2013 | Wang et al. |
| 2013/0131499 A1 | 5/2013 | Chan et al. |
| 2013/0131641 A1 | 5/2013 | Jimenez et al. |
| 2013/0131710 A1 | 5/2013 | Carmeli et al. |
| 2013/0144328 A1 | 6/2013 | Weber et al. |
| 2013/0158511 A1 | 6/2013 | Aggerholm et al. |
| 2013/0158578 A1 | 6/2013 | Ghodke et al. |
| 2013/0214912 A1 | 8/2013 | Beyar et al. |
| 2013/0231678 A1 | 9/2013 | Wenderow |
| 2013/0325055 A1 | 12/2013 | Eckhouse et al. |
| 2014/0025043 A1 | 1/2014 | Wang et al. |
| 2014/0039461 A1 | 2/2014 | Anderson et al. |
| 2014/0046243 A1 | 2/2014 | Ray et al. |
| 2014/0046244 A1 | 2/2014 | Ray et al. |
| 2014/0058321 A1 | 2/2014 | Wenderow et al. |
| 2014/0066900 A1 | 3/2014 | Blacker |
| 2014/0074144 A1 | 3/2014 | Shrivastava et al. |
| 2014/0114287 A1 | 4/2014 | Beasley et al. |
| 2014/0118931 A1 | 5/2014 | Hata |
| 2014/0121555 A1 | 5/2014 | Scott et al. |
| 2014/0121746 A1 | 5/2014 | Kusleika et al. |
| 2014/0150782 A1 | 6/2014 | Vazales |
| 2014/0155932 A1 | 6/2014 | Bose et al. |
| 2014/0155980 A1 | 6/2014 | Turjman et al. |
| 2014/0163364 A1 | 6/2014 | Perers |
| 2014/0163367 A1 | 6/2014 | Eskuri |
| 2014/0200608 A1 | 7/2014 | Brady et al. |
| 2014/0216250 A1 | 8/2014 | Meyer |
| 2014/0228762 A1 | 8/2014 | Capone |
| 2014/0228808 A1 | 8/2014 | Webster et al. |
| 2014/0243742 A1 | 8/2014 | Pacheco et al. |
| 2014/0243882 A1 | 8/2014 | Ma |
| 2014/0249508 A1 | 9/2014 | Wang et al. |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276016 A1 | 9/2014 | Stigall |
| 2014/0276167 A1 | 9/2014 | Dasgupta et al. |
| 2014/0276233 A1 | 9/2014 | Murphy |
| 2014/0276389 A1 | 9/2014 | Walker |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0276948 A1 | 9/2014 | Zirps |
| 2014/0277003 A1 | 9/2014 | Hendrick |
| 2014/0288525 A1 | 9/2014 | Fudaba et al. |
| 2014/0296889 A1 | 10/2014 | Avneri et al. |
| 2014/0309533 A1 | 10/2014 | Yamashita et al. |
| 2014/0318702 A1 | 10/2014 | Tegg |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2014/0371718 A1 | 12/2014 | Alvarez et al. |
| 2015/0005704 A1 | 1/2015 | Heisel et al. |
| 2015/0005738 A1 | 1/2015 | Blacker |
| 2015/0005745 A1 | 1/2015 | Bergman et al. |
| 2015/0046148 A1 | 2/2015 | Oh et al. |
| 2015/0073391 A1 | 3/2015 | Hutchins et al. |
| 2015/0088002 A1 | 3/2015 | Podhajsky et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0157252 A1 | 6/2015 | Sabesan |
| 2015/0157772 A1 | 6/2015 | Li et al. |
| 2015/0173782 A1 | 6/2015 | Garrison et al. |
| 2015/0174363 A1 | 6/2015 | Sutermeister et al. |
| 2015/0174368 A1 | 6/2015 | Garrison et al. |
| 2015/0257659 A1 | 9/2015 | Broers et al. |
| 2015/0272683 A1 | 10/2015 | Yang et al. |
| 2015/0290390 A1 | 10/2015 | Ring et al. |
| 2015/0314105 A1 | 11/2015 | Gasparyan |
| 2015/0327875 A1 | 11/2015 | Look |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2015/0374483 A1 | 12/2015 | Janardhan |
| 2016/0000443 A1 | 1/2016 | Lilburn et al. |
| 2016/0008572 A1 | 1/2016 | Di Capriov |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0184032 A1 | 6/2016 | Romo |
| 2016/0199204 A1 | 7/2016 | Pung et al. |
| 2016/0199620 A1 | 7/2016 | Pokorney et al. |
| 2016/0206216 A1 | 7/2016 | Kirenko |
| 2016/0206322 A1 | 7/2016 | Fitz et al. |
| 2016/0213396 A1 | 7/2016 | Dowell et al. |
| 2016/0220265 A1 | 8/2016 | Pokorney et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |

(56)                    References Cited

U.S. PATENT DOCUMENTS

| | | |
|---|---|---|
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0310702 A1 | 10/2016 | Cabiri |
| 2016/0311990 A1 | 10/2016 | Cruise et al. |
| 2016/0317156 A1 | 11/2016 | Fitz et al. |
| 2016/0317173 A1 | 11/2016 | Hendrick |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0354532 A1 | 12/2016 | Olesky et al. |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2016/0374590 A1 | 12/2016 | Wong et al. |
| 2017/0000576 A1 | 1/2017 | Zirps |
| 2017/0007264 A1 | 1/2017 | Cruise et al. |
| 2017/0007277 A1 | 1/2017 | Drapeau et al. |
| 2017/0014998 A1 | 1/2017 | Langenfeld et al. |
| 2017/0020540 A1 | 1/2017 | Chou et al. |
| 2017/0020627 A1 | 1/2017 | Tesar et al. |
| 2017/0021172 A1 | 1/2017 | Perez et al. |
| 2017/0027604 A1 | 2/2017 | Wallace |
| 2017/0027653 A1 | 2/2017 | Kirschenman |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0043124 A1 | 2/2017 | Vreeman |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0135773 A1 | 5/2017 | Lohmeier et al. |
| 2017/0143416 A1 | 5/2017 | Guler et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224224 A1 | 8/2017 | Yu |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0246014 A1 | 8/2017 | Rapaport et al. |
| 2017/0252025 A1 | 9/2017 | Cabiri et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281054 A1 | 10/2017 | Stever et al. |
| 2017/0281192 A1 | 10/2017 | Tieu et al. |
| 2017/0281204 A1 | 10/2017 | Garrison et al. |
| 2017/0281288 A1 | 10/2017 | Au |
| 2017/0283536 A1 | 10/2017 | Cruise et al. |
| 2017/0303949 A1 | 10/2017 | Jacobi et al. |
| 2017/0317937 A1 | 11/2017 | Dillon |
| 2017/0333000 A1 | 11/2017 | Nystrom et al. |
| 2017/0340867 A1 | 11/2017 | Accisano |
| 2017/0348060 A1 | 12/2017 | Blacker |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0104390 A1 | 4/2018 | Kilcran |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1 | 6/2018 | Yi et al. |
| 2018/0169508 A1 | 6/2018 | Billardello et al. |
| 2018/0185104 A1 | 7/2018 | Olson et al. |
| 2018/0199916 A1 | 7/2018 | Sugihara et al. |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0228502 A1 | 8/2018 | Shaffer et al. |
| 2018/0242962 A1 | 8/2018 | Walen et al. |
| 2018/0242980 A1 | 8/2018 | Lubock et al. |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0250086 A1 | 9/2018 | Grubbs |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2018/0304040 A1 | 10/2018 | Jalgaonkar |
| 2018/0307362 A1 | 10/2018 | Komala et al. |
| 2018/0353194 A1 | 12/2018 | Shaffer et al. |
| 2018/0360398 A1 | 12/2018 | Wenderow et al. |
| 2019/0008360 A1 | 1/2019 | Peh et al. |
| 2019/0008591 A1 | 1/2019 | Desai |
| 2019/0022363 A1 | 1/2019 | Grayzel et al. |
| 2019/0029825 A1 | 1/2019 | Fitterer et al. |
| 2019/0030305 A1 | 1/2019 | Aboytes |
| 2019/0030324 A1 | 1/2019 | Grace et al. |
| 2019/0070387 A1 | 3/2019 | Goyal |
| 2019/0076640 A1 | 3/2019 | Bhatnagar et al. |
| 2019/0108540 A1 | 4/2019 | Look et al. |
| 2019/0111237 A1 | 4/2019 | Cabiri et al. |
| 2019/0125393 A1 | 5/2019 | Hendrick |
| 2019/0133666 A1 | 5/2019 | Johnson |
| 2019/0167124 A1 | 6/2019 | Verkruijsse et al. |
| 2019/0175030 A1 | 6/2019 | Verkruijsse et al. |
| 2019/0183517 A1 | 6/2019 | Ogle |
| 2019/0200871 A1 | 7/2019 | De Haan |
| 2019/0209026 A1 | 7/2019 | Han et al. |
| 2019/0231373 A1 | 8/2019 | Quick |
| 2019/0239910 A1 | 8/2019 | Brade et al. |
| 2019/0254690 A1 | 8/2019 | Cabiri et al. |
| 2019/0254754 A1 | 8/2019 | Johnson |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0275290 A1 | 9/2019 | Yamashita et al. |
| 2019/0290884 A1 | 9/2019 | Kanemasa et al. |
| 2019/0301913 A1 | 10/2019 | Johnson |
| 2019/0304108 A1 | 10/2019 | Carrell et al. |
| 2019/0329003 A1 | 10/2019 | Watanabe |

(56) References Cited

U.S. PATENT DOCUMENTS

| | | |
|---|---|---|
| 2019/0336142 A1 | 11/2019 | Torrie |
| 2019/0336227 A1 | 11/2019 | Murphy et al. |
| 2019/0336674 A1 | 11/2019 | Schermeier |
| 2019/0351182 A1 | 11/2019 | Chou et al. |
| 2019/0365485 A1 | 12/2019 | Kottenstette |
| 2019/0380825 A1 | 12/2019 | Perkins et al. |
| 2020/0001046 A1 | 1/2020 | Yang et al. |
| 2020/0008820 A1 | 1/2020 | Aboytes et al. |
| 2020/0008891 A1 | 1/2020 | Wenderow et al. |
| 2020/0008896 A1 | 1/2020 | Cone et al. |
| 2020/0009301 A1 | 1/2020 | Yee |
| 2020/0009350 A1 | 1/2020 | Goyal |
| 2020/0009354 A1 | 1/2020 | Wenderow et al. |
| 2020/0016371 A1 | 1/2020 | Blacker |
| 2020/0022712 A1 | 1/2020 | Deville et al. |
| 2020/0023160 A1 | 1/2020 | Chou et al. |
| 2020/0025845 A1 | 1/2020 | Ferguson et al. |
| 2020/0028181 A1 | 1/2020 | Arugula et al. |
| 2020/0046368 A1 | 2/2020 | Merritt et al. |
| 2020/0046937 A1 | 2/2020 | Nakagawa et al. |
| 2020/0054403 A1 | 2/2020 | Zhou et al. |
| 2020/0085528 A1 | 3/2020 | Olson et al. |
| 2020/0129740 A1 | 4/2020 | Kottenstette et al. |
| 2020/0163726 A1 | 5/2020 | Tanner et al. |
| 2020/0170521 A1 | 6/2020 | Gupta et al. |
| 2020/0170630 A1 | 6/2020 | Wong et al. |
| 2020/0171276 A1 | 6/2020 | Onozuka |
| 2020/0171277 A1 | 6/2020 | Garrison et al. |
| 2020/0187979 A1 | 6/2020 | Bowman |
| 2020/0188630 A1 | 6/2020 | Fujita et al. |
| 2020/0205845 A1 | 7/2020 | Yang et al. |
| 2020/0242767 A1 | 7/2020 | Zhao et al. |
| 2020/0276411 A1 | 9/2020 | Ogle et al. |
| 2020/0282186 A1 | 9/2020 | Blacker et al. |
| 2020/0289136 A1 | 9/2020 | Chou |
| 2020/0289219 A1 | 9/2020 | Denlinger et al. |
| 2020/0297362 A1 | 9/2020 | Deville et al. |
| 2020/0297444 A1 | 9/2020 | Camarillo et al. |
| 2020/0297972 A1 | 9/2020 | Yee et al. |
| 2020/0297973 A1 | 9/2020 | Blacker et al. |
| 2020/0306064 A1 | 10/2020 | Perkins et al. |
| 2020/0306501 A1 | 10/2020 | Yee et al. |
| 2020/0316340 A1 | 10/2020 | Wenderow et al. |
| 2020/0323535 A1 | 10/2020 | Yang et al. |
| 2020/0324084 A1 | 10/2020 | Falb et al. |
| 2020/0337716 A1 | 10/2020 | Garrison et al. |
| 2020/0338308 A1 | 10/2020 | Saber et al. |
| 2020/0345979 A1 | 11/2020 | Loh et al. |
| 2020/0352494 A1 | 11/2020 | Gable et al. |
| 2020/0368494 A1 | 11/2020 | Parmar |
| 2020/0375671 A1 | 12/2020 | Wenderow et al. |
| 2020/0376249 A1 | 12/2020 | Lockhart |
| 2020/0390503 A1 | 12/2020 | Casas et al. |
| 2020/0397451 A1 | 12/2020 | Feltyberger et al. |
| 2020/0405408 A1 | 12/2020 | Shelton, IV et al. |
| 2020/0405410 A1 | 12/2020 | Shelton, IV et al. |
| 2020/0405950 A1 | 12/2020 | Burren |
| 2021/0001141 A1 | 1/2021 | Pfiffner et al. |
| 2021/0007816 A1 | 1/2021 | Huang et al. |
| 2021/0022816 A1 | 1/2021 | DeBuys et al. |
| 2021/0030492 A1 | 2/2021 | Wenderow et al. |
| 2021/0045622 A1 | 2/2021 | Petroff et al. |
| 2021/0045758 A1 | 2/2021 | Garrison et al. |
| 2021/0046284 A1 | 2/2021 | Mauch |
| 2021/0052296 A1 | 2/2021 | Garrison |
| 2021/0060767 A1 | 3/2021 | Guerrera et al. |
| 2021/0068852 A1 | 3/2021 | Spence |
| 2021/0077211 A1 | 3/2021 | Blacker et al. |
| 2021/0093336 A1 | 4/2021 | Roue |
| 2021/0093406 A1 | 4/2021 | Blacker et al. |
| 2021/0100980 A1 | 4/2021 | Blacker |
| 2021/0106792 A1 | 4/2021 | Rafiee |
| 2021/0128182 A1 | 5/2021 | Teigen et al. |
| 2021/0145532 A1 | 5/2021 | Tucker et al. |
| 2021/0146094 A1 | 5/2021 | Christian et al. |
| 2021/0153744 A1 | 5/2021 | Pierro |
| 2021/0178032 A1 | 6/2021 | Hsu et al. |
| 2021/0178036 A1 | 6/2021 | Nazarifar et al. |
| 2021/0186534 A1 | 6/2021 | Hunt et al. |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0192759 A1 | 6/2021 | Lang |
| 2021/0196242 A1 | 7/2021 | Perez |
| 2021/0196413 A1 | 7/2021 | Inoue |
| 2021/0212792 A1 | 7/2021 | Shelton et al. |
| 2021/0220064 A1 | 7/2021 | Kottenstette et al. |
| 2021/0228841 A1 | 7/2021 | Falb et al. |
| 2021/0244434 A1 | 8/2021 | Popa et al. |
| 2021/0247396 A9 | 8/2021 | Penny et al. |
| 2021/0251472 A1 | 8/2021 | Baez |
| 2021/0259884 A1 | 8/2021 | Heeren et al. |
| 2021/0282863 A1 | 9/2021 | Rafii-Tari et al. |
| 2021/0282867 A1 | 9/2021 | Tegg et al. |
| 2021/0282875 A1 | 9/2021 | Sharon et al. |
| 2021/0282893 A1 | 9/2021 | Leo et al. |
| 2021/0290310 A1 | 9/2021 | Laby et al. |
| 2021/0290320 A1 | 9/2021 | Mao et al. |
| 2021/0290324 A1 | 9/2021 | Mintz et al. |
| 2021/0298847 A1 | 9/2021 | Mao et al. |
| 2021/0298850 A1 | 9/2021 | Huang et al. |
| 2021/0298857 A1 | 9/2021 | Zheng et al. |
| 2021/0298954 A1 | 9/2021 | Alvarez et al. |
| 2021/0305639 A1 | 9/2021 | Ho et al. |
| 2021/0307767 A1 | 10/2021 | Gifford, III et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |
| 2021/0353129 A1 | 11/2021 | Roelle et al. |
| 2021/0361366 A1 | 11/2021 | Murphy et al. |
| 2021/0361909 A1 | 11/2021 | Cottone et al. |
| 2021/0369370 A1 | 12/2021 | Malanoski |
| 2021/0378527 A1 | 12/2021 | Strasser et al. |
| 2021/0378696 A1 | 12/2021 | Yang et al. |
| 2021/0393275 A1 | 12/2021 | Whelan |
| 2021/0393276 A1 | 12/2021 | Whelan |
| 2021/0393338 A1 | 12/2021 | Graetzel et al. |
| 2021/0401527 A1 | 12/2021 | Hassan |
| 2022/0031415 A1 | 2/2022 | Vargas et al. |
| 2022/0040450 A1 | 2/2022 | Haubert |
| 2022/0047849 A1 | 2/2022 | Yee et al. |
| 2022/0080158 A1 | 3/2022 | McLaughlin et al. |
| 2022/0151646 A1 | 5/2022 | Dholakia et al. |
| 2022/0167984 A1 | 6/2022 | Shelton, IV |
| 2022/0168000 A1 | 6/2022 | Naglretter et al. |
| 2022/0168001 A1 | 6/2022 | Naglretter et al. |
| 2022/0168002 A1 | 6/2022 | Naglretter et al. |
| 2022/0168010 A1 | 6/2022 | Brinkmann et al. |
| 2022/0168049 A1 | 6/2022 | Tanner et al. |
| 2022/0211452 A1 | 7/2022 | Clark et al. |
| 2022/0211975 A1 | 7/2022 | Yang et al. |
| 2022/0233263 A1* | 7/2022 | Canale ............... A61B 1/00147 |
| 2022/0233264 A1 | 7/2022 | Klem |
| 2022/0233820 A1 | 7/2022 | Clark et al. |
| 2022/0241490 A1 | 8/2022 | Marass |
| 2022/0287785 A1 | 9/2022 | Hassan et al. |
| 2022/0313375 A1 | 10/2022 | Zhang et al. |
| 2022/0323096 A1 | 10/2022 | Naglretter et al. |
| 2022/0330960 A1 | 10/2022 | Buck et al. |
| 2022/0331085 A1 | 10/2022 | Buck et al. |
| 2022/0331509 A1 | 10/2022 | Buck et al. |
| 2022/0370161 A1 | 11/2022 | Yu |
| 2022/0370706 A1 | 11/2022 | Meganck |
| 2022/0378522 A1 | 12/2022 | Zemlok et al. |
| 2023/0000563 A1 | 1/2023 | Bell et al. |
| 2023/0035508 A1 | 2/2023 | Clark et al. |
| 2023/0035946 A1 | 2/2023 | Kapadia |
| 2023/0043432 A1 | 2/2023 | Kapadia |
| 2023/0046468 A1 | 2/2023 | Lau et al. |
| 2023/0048055 A1 | 2/2023 | Lau et al. |
| 2023/0048388 A1 | 2/2023 | Lau et al. |
| 2023/0052862 A1 | 2/2023 | Lau et al. |

(56) References Cited

U.S. PATENT DOCUMENTS

| | | | |
|---|---|---|---|
| 2023/0107693 A1 | 4/2023 | Walker et al. |
| 2023/0116327 A1 | 4/2023 | Walker et al. |
| 2023/0116700 A1 | 4/2023 | Yu et al. |
| 2023/0117715 A1 | 4/2023 | Ho et al. |
| 2023/0126545 A1 | 4/2023 | Liu et al. |
| 2023/0202040 A1 | 6/2023 | Lin et al. |
| 2023/0218816 A1 | 7/2023 | Germain et al. |
| 2023/0310100 A1 | 10/2023 | Wenderow et al. |
| 2023/0347110 A1 | 11/2023 | Wenderow et al. |
| 2024/0001101 A1 | 1/2024 | Wallin et al. |
| 2024/0016560 A1 | 1/2024 | Canale et al. |
| 2024/0019042 A1 | 1/2024 | Lim |
| 2024/0032949 A1 | 2/2024 | Yang et al. |
| 2024/0033016 A1 | 2/2024 | Yang et al. |
| 2024/0033017 A1 | 2/2024 | Yang et al. |
| 2024/0033018 A1 | 2/2024 | Yang et al. |
| 2024/0033019 A1 | 2/2024 | Lau et al. |
| 2024/0033486 A1 | 2/2024 | Lau et al. |
| 2024/0041480 A1 | 2/2024 | Bartholomew |
| 2024/0042124 A1 | 2/2024 | Bartholomew |
| 2024/0042142 A1 | 2/2024 | Bartholomew |
| 2024/0122612 A1 | 4/2024 | Bartholomew |
| 2024/0165415 A1 | 5/2024 | Grosskopf et al. |
| 2024/0180635 A1 | 6/2024 | Lau et al. |
| 2024/0180640 A1 | 6/2024 | Lau et al. |
| 2024/0180641 A1 | 6/2024 | Lau et al. |
| 2024/0180642 A1 | 6/2024 | Lau et al. |
| 2024/0180643 A1 | 6/2024 | Lau et al. |
| 2024/0180650 A1 | 6/2024 | Lau et al. |
| 2024/0180651 A1 | 6/2024 | Lau et al. |
| 2024/0180652 A1 | 6/2024 | Lau et al. |
| 2024/0180653 A1 | 6/2024 | Lau et al. |
| 2024/0180654 A1 | 6/2024 | Lau et al. |
| 2024/0180658 A1 | 6/2024 | Lau et al. |
| 2024/0180659 A1 | 6/2024 | Lau et al. |
| 2024/0181207 A1 | 6/2024 | Lau et al. |
| 2024/0181208 A1 | 6/2024 | Lau et al. |
| 2024/0181213 A1 | 6/2024 | Lau et al. |
| 2024/0181214 A1 | 6/2024 | Lau et al. |
| 2024/0181224 A1 | 6/2024 | Lau et al. |
| 2024/0181298 A1 | 6/2024 | Lau et al. |
| 2024/0183382 A1 | 6/2024 | Lau et al. |
| 2024/0197416 A1 | 6/2024 | Gonzalez |
| 2024/0197418 A1 | 6/2024 | Jourdan |
| 2024/0198051 A1 | 6/2024 | Jourdan |
| 2024/0207570 A1 | 6/2024 | Mar |
| 2024/0382668 A1 | 11/2024 | Bartholomew et al. |
| 2024/0398495 A1 | 12/2024 | Lee et al. |
| 2025/0032201 A1 | 1/2025 | Bartholomew et al. |
| 2025/0195835 A1 | 6/2025 | Totten |

FOREIGN PATENT DOCUMENTS

| | | | |
|---|---|---|---|
| CN | 101123918 A | 2/2008 |
| CN | 101252958 A | 8/2008 |
| CN | 101321552 A | 12/2008 |
| CN | 101340849 A | 1/2009 |
| CN | 101795631 A | 8/2010 |
| CN | 201596219 U | 10/2010 |
| CN | 102205161 | 10/2011 |
| CN | 102319097 A | 1/2012 |
| CN | 102462533 | 5/2012 |
| CN | 102573701 A | 7/2012 |
| CN | 102844071 A | 12/2012 |
| CN | 102847220 A | 1/2013 |
| CN | 203263993 U | 11/2013 |
| CN | 103648574 A | 3/2014 |
| CN | 103764214 A | 4/2014 |
| CN | 103976766 | 8/2014 |
| CN | 104042259 | 9/2014 |
| CN | 203935213 | 11/2014 |
| CN | 204158457 U | 2/2015 |
| CN | 104548316 A | 4/2015 |
| CN | 104622538 A | 5/2015 |
| CN | 204428157 | 7/2015 |
| CN | 105120776 A | 12/2015 |
| CN | 105208951 A | 12/2015 |
| CN | 204909516 U | 12/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |
| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107405159 A | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 | 5/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 110916768 | 3/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| DE | 8900059 | 5/1989 |
| DE | 10 2010 053111 | 6/2012 |
| DE | 10 2012 112732 | 6/2014 |
| EP | 0 330 843 | 12/1993 |
| EP | 0 582 533 | 2/1994 |
| EP | 0 309 471 | 8/1996 |
| EP | 1 776 057 B1 | 4/2007 |
| EP | 1 349 486 | 3/2008 |
| EP | 2 069 528 | 3/2013 |

(56) References Cited

FOREIGN PATENT DOCUMENTS

| | | |
|---|---|---|
| EP | 2 937 108 | 10/2015 |
| EP | 2 928 360 | 1/2017 |
| EP | 2 211 732 | 5/2018 |
| EP | 2 124 705 B1 | 5/2019 |
| EP | 3 539 486 | 9/2019 |
| EP | 3 698 740 | 8/2020 |
| FR | 3118406 | 7/2022 |
| GB | 2077132 | 12/1981 |
| JP | 2002-535049 | 10/2002 |
| JP | 2003-527925 | 9/2003 |
| JP | 2006-087643 | 4/2006 |
| JP | 2006-102222 | 4/2006 |
| JP | 2006-521881 | 9/2006 |
| JP | 2008-502378 | 1/2008 |
| JP | 2013-504388 | 2/2013 |
| JP | 2014-515670 | 7/2014 |
| JP | 2015-504327 | 2/2015 |
| WO | WO 1995/009659 | 4/1995 |
| WO | WO 2000/000100 | 1/2000 |
| WO | WO 2006/101170 | 9/2006 |
| WO | WO 2007/102134 | 9/2007 |
| WO | WO 2008/057887 | 10/2008 |
| WO | WO 2009/054968 | 4/2009 |
| WO | WO 09/125575 | 10/2009 |
| WO | WO 2009/132218 | 10/2009 |
| WO | WO 2010/126786 | 11/2010 |
| WO | WO 2013/103885 | 7/2013 |
| WO | WO 2014/151209 | 9/2014 |
| WO | WO 2014/203336 | 12/2014 |
| WO | WO 2016/001712 | 1/2016 |
| WO | WO 2016/191307 | 12/2016 |
| WO | WO 2017/025775 | 2/2017 |
| WO | WO 2017/220010 | 12/2017 |
| WO | WO 2018/121363 | 7/2018 |
| WO | WO 18/169032 | 9/2018 |
| WO | WO 2019/178165 | 9/2019 |
| WO | WO 2019/222518 | 11/2019 |
| WO | WO 2019/222641 | 11/2019 |
| WO | WO 2019/246583 | 12/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2020/145928 | 7/2020 |
| WO | WO 2021/011551 | 7/2020 |
| WO | WO 2020/167749 | 8/2020 |
| WO | WO 20/263630 | 12/2020 |
| WO | WO 2021/011533 | 1/2021 |
| WO | WO 2021/011554 | 1/2021 |
| WO | WO 2021/015990 | 1/2021 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2021/242734 | 12/2021 |
| WO | WO 2022/048984 | 3/2022 |
| WO | WO 2022/154979 | 7/2022 |
| WO | WO 2022/220899 | 10/2022 |

OTHER PUBLICATIONS

US 12,108,960 B1, 10/2024, Teigen et al. (withdrawn)
Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.
Bao et al., Apr. 2018, Operation evaluation in-human of a novel remote-controlled vascular interventional robot, Biomedical Microdevices, 20(2):34.
Bao et al., Feb. 2018, A cooperation of catheters and guidewires-based novel remote-controlled vascular interventional robot, Biomedical Microdevices, 20(1):20.
Bergman et al., 2020, Robotic-assisted percutaneous coronary intervention, Handbook of Robotic and Image-Guided Surgery, doi: https://doi.org/10.1016/B978-0-12-814245-5.00020-7.
GUIDEZILLA Guide Extension Catheter, Boston Scientific 510k Submission, Feb. 20, 2017.
Guo et al., Apr. 13, 2018, Study on real-time force feedback for a master-slave interventional surgical robotic system, Biomedical Microdevices, 20(2):37, 12 pp.
Jiang et al., 2018, Initial clinical trial of robot of endovascular treatment with force feedback and cooperating of catheter and guidewire, Applied Bionics and Biomechanics, vol. 2018, Article ID 9735979, 10 pp.
Kagiyama et al., Jul. 31, 2019, First experience of robotic-assisted percutaneous coronary intervention in Japan, Intern Med Advance Publication, doi: 10/2016/internalmedicine.3272-19.
Korpelainen et al., 1995, Asymmetrical skin temperature in ischemic stroke, Stroke, 26(9):1543-1547.
Liu et al., 2021, Animal experiment of a novel neurointerventional surgical robotic system with master- slave mode, Applied Bionics and Biomechanics, vol. 2021, Article ID 8836268, 8 pp.
Merit Medical Systems Acquired Distal Access's SPINR Platform, Jul. 15, 2015, Digital Access, LLC; Merit Medical Systems, 5 pages.
Simon et al., Exploring the efficacy of cyclic vs. static aspiration in a cerebral thrombectomy model: an initial proof of concept study, J. NeuroIntervent Surg 2014, 6 pp. 677-683.
Simon et al., Hydrodynamic comparison of the Penumbra system and commonly available syringes in forced-suction thrombectomy, J. NeuroIntervent Surg 2014, 6, pp. 205-211.
Spiotta et al., Evolution of thrombectomy approaches and devices for acute stroke: a technical review, J. NeuroIntervent Surg 2015, 7, pp. 2-7.
Wang et al., Feb. 3, 2018, Online measuring and evaluation of guidewire inserting resistance for robotic interventional surgery systems, Microsystem Technologies, https://doi/org/10.1007/s00542-018-03750-4.
Zhao et al., Apr. 2, 2018, Operating force information on-line acquisition of a novel slave manipulator for vascular interventional surgery, Biomedical Microdevices, 20(2):33, 13 pp.
Zhou et al., 2021, ADRC-based control method for the vascular intervention master-slave surgical robotic system, Micromachines, 12:1439.
Bell, Apr. 4, 2019, Coding for Empathy, https://www.youtube.com/watch?v=13tzbxofDVc, screenshot of video.
Bency et al., Apr. 25, 2019, Neural Path Planning: Fixed Time, Near-Optimal Path Generation via Oracle Imitation, arXiv:1904.11102v1 [cs.RO], 8 pp.
Chen et al., Feb. 14, 2020, Deep learning robotic guidance for autonomous vascular access, Nature Machine Intelligence, https://doi.org/10.1038/s42256-020-0148-7, 12 pp.
Das et al., Feb. 21, 2019, Learning-Based Proxy Collision Detection for Robot Motion Planning Applications, arXiv: 1902.08164v1 [cs.RO], 19 pp.
Das et al., May 29, 2020, Stochastic Modeling of Distance to Collision for Robot Manipulators, arXiv:2005.14391v1 [cs. RO], 8 pp.
Fagogenis et al., Apr. 2019, Autonomous Robotic Intracardiac Catheter Navigation Using Haptic Vision, Science Robotics, 4(29):1-12.
Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.
Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

(56)　　　　　References Cited

OTHER PUBLICATIONS

Johnson et al., Aug. 12, 2020, Dynamically Constrained Motion Planning Networks for Non-Holonomic Robots, arXiv:2008. 05112v1 [cs.RO}, 7 pp.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/ Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

Yip et al., Jul. 10, 2017, Robot Autonomy for Surgery, https://arxiv. org/pdf/1707.03080.pdf, 33 pp.

Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.

International Search Report and Written Opinion dated Nov. 23, 2022 in application No. PCT/US2022/074688.

International Search Report and Written Opinion dated Dec. 6, 2022 in application No. PCT/US2022/074681.

International Search Report and Written Opinion dated Nov. 16, 2022 in application No. PCT/US2022/074682.

Evard, Jun. 2018, Catheter localization utilizing a sensor-enabled guidewire design of a proof-of- concept system, Masters' Thesis, California Polytechnic State University, San Luis Obispo, 186 pp.

Bergam et al., 2020, Robotic assisted percutaneous coronary interventions, in Handbook of Robotic and Image Guided Surgery, Elsevier Inc., pp. 341-362.

* cited by examiner

Side view of puck and carriage
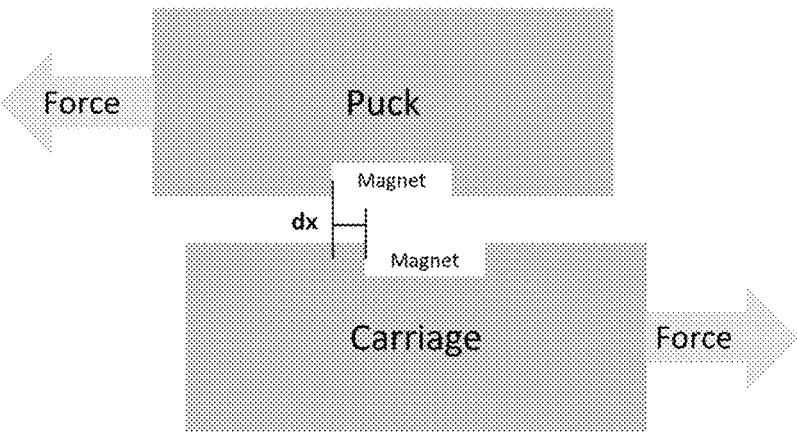
FIG. 13A
Equivalent System
Puck —WWW— Carriage
k
Spring
FIG. 13B
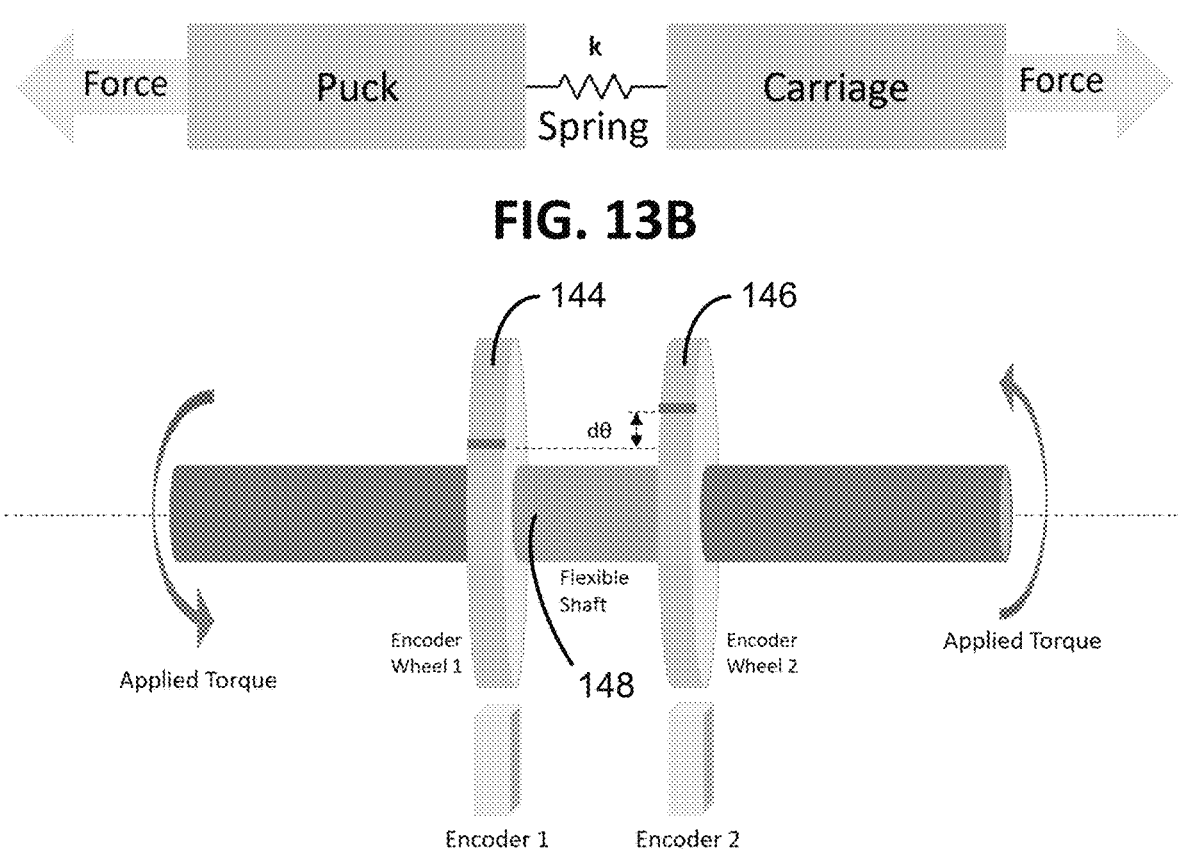
FIG. 14

MULTI CATHETER METHOD OF PERFORMING A ROBOTIC NEUROVASCULAR PROCEDURE

CROSS-REFERENCE TO RELATED APPLICATIONS

This application claims the benefit of U.S. Provisional Application No. 63/232,444, filed Aug. 12, 2021, the entirety of this application is hereby incorporated by reference herein.

BACKGROUND OF THE INVENTION

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to frictional interplay between coaxial shafts and the patient's vasculature. Supra-aortic access necessary to reach the neurovascular is challenging to achieve, especially Type III arches.

Thus, there remains a need for a supra-aortic access system that addresses some or all of these challenges, and increases the availability of neurovascular procedures. Preferably, the system is additionally capable of driving devices further distally through the supra-aortic access to accomplish procedures in the intracranial vessels.

SUMMARY OF THE INVENTION

There is provided in accordance with one aspect of the present invention a supra-aortic access robotic control system. The system comprises a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter, and also to laterally deflect a distal deflection zone of the access catheter. The guidewire hub may additionally be configured to laterally deflect a distal portion of the guidewire.

There may also be provided a procedure catheter hub configured to manipulate a procedure catheter. Following robotic placement of the guidewire, access catheter and guide catheter such that the guide catheter achieves supra-aortic access, the guidewire and access catheter may be proximally withdrawn, and the procedure catheter advanced through and beyond the guide catheter to reach a neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, a balloon catheter or a stent retriever.

The control system may further comprise a driven magnet on each of a guidewire hub, an access catheter hub, and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may comprise a tray made from a thin polymer membrane, or any membrane of non-ferromagnetic material.

The control system may further comprise a control console which may be connected to the support table or may be located remotely from the support table. The position of each driven magnet and corresponding hub is movable in response to manual manipulation of a guidewire drive control, access catheter drive control or procedure catheter drive control on the console.

The control system may further comprise a processor for controlling the position of the drive magnets. The processor may be in wired communication with the control console, or in wireless communication with the control console. The driven magnets may be configured to remain engaged with the corresponding drive magnets until application of a disruption force of at least about 300 grams.

There is also provided a robotically driven interventional device. The device comprises an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. The control element may be an axially movable tubular body or wire such as a pull wire extending through the interventional device to, for example, a distal deflection zone.

There is also provided a control system for controlling movement of interventional devices. In one configuration, the control system comprises a guidewire control, configured to control axial travel and rotation of a guidewire; an access catheter control, configured to control axial and rotational movement of an access catheter; and a guide catheter control, configured to control axial movement of a guide catheter.

The control system may further comprise a deflection control, configured to control deflection of the access catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further comprise a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further comprise a graphical user interface with at least one display for indicating the status of at least one device parameter, and/or indicating the status of at least one patient parameter.

There is also provided a sterile packaging assembly for transporting interventional devices to a robotic surgery site. The packaging assembly may comprise a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient, with an upper surface of the base within a sterile field and a lower surface of the base outside of the sterile field.

Any of the hubs disclosed herein may further comprises a fluid injection port and/or a wireless RF transceiver. The hub may comprise a visual indicator, for indicating the presence of a clot. The visual indicator may comprise a clot chamber having a transparent window. A filter may be provided in the clot chamber.

Any of the hubs disclosed herein may further comprise a sensor for detecting a parameter of interest such as the presence of a clot. The sensor, in some instances, may be positioned on a flexible body. The sensor may comprise a pressure sensor or an optical sensor. In some embodiments, the sensor may comprise one or more of a force sensor, a temperature sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each comprise one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method comprises the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally comprise advancing the procedure catheter hub to position a distal end of the procedure catheter at a neurovascular treatment site. The driving the access catheter step may comprise driving the access catheter distally through a guide catheter. The driving the access catheter step may include the step of laterally deflecting a distal region of the access catheter to achieve supra-aortic access.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guide wire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may comprise magnetically coupling a hub on each of the guidewire, access catheter and guide catheter, to separate corresponding couplers carrying corresponding drive magnets independently movably carried by the drive table. The procedure assembly may comprise a guidewire, a first catheter and a second catheter. The guidewire and first catheter may be positioned concentrically within the second catheter. The procedure assembly may be advanced as a unit through at least a portion of the length of the guide catheter, and the procedure may comprise a neurovascular thrombectomy.

Additional features and advantages of the present invention are disclosed in Appendix A and Appendix B to U.S. Provisional Application No. 63/232,444, the entirety of each of which is hereby incorporated by reference herein.

BRIEF DESCRIPTION OF THE DRAWINGS

FIGS. 13A and 13B schematically illustrate a sensor for measuring elastic forces at the magnetic coupling between the hub and corresponding carriage.

FIG. 14 schematically illustrates a dual encoder torque sensor for use with a catheter of the present invention.

DETAILED DESCRIPTION OF THE PREFERRED EMBODIMENT

The present invention provides a system for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations of the invention, the system may additionally be configured to robotically gain intracranial vascular access and to perform an aspiration thrombectomy or other neuro vascular procedure.

A drive table is positioned over or alongside the patient, and configured to axially advance, retract, and in some cases rotate and/or laterally deflect two or three or more different (e.g., concentrically or side by side oriented) intravascular devices. Each device has a proximal end attached to a unique hub, sometimes referred to as a "puck". The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub is in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device approximately or distally within the patient's vasculature.

The carriages on the drive table which magnetically couple with the hubs to provides linear motion actuation are universal. Functionality of the catheters/guidewire are provided based on what is contained in the hubs and the shaft designs. This allows flexibility to configure the system to do a wide range of procedures using a wide variety of interventional devices on the same drive table.

Figure 1:
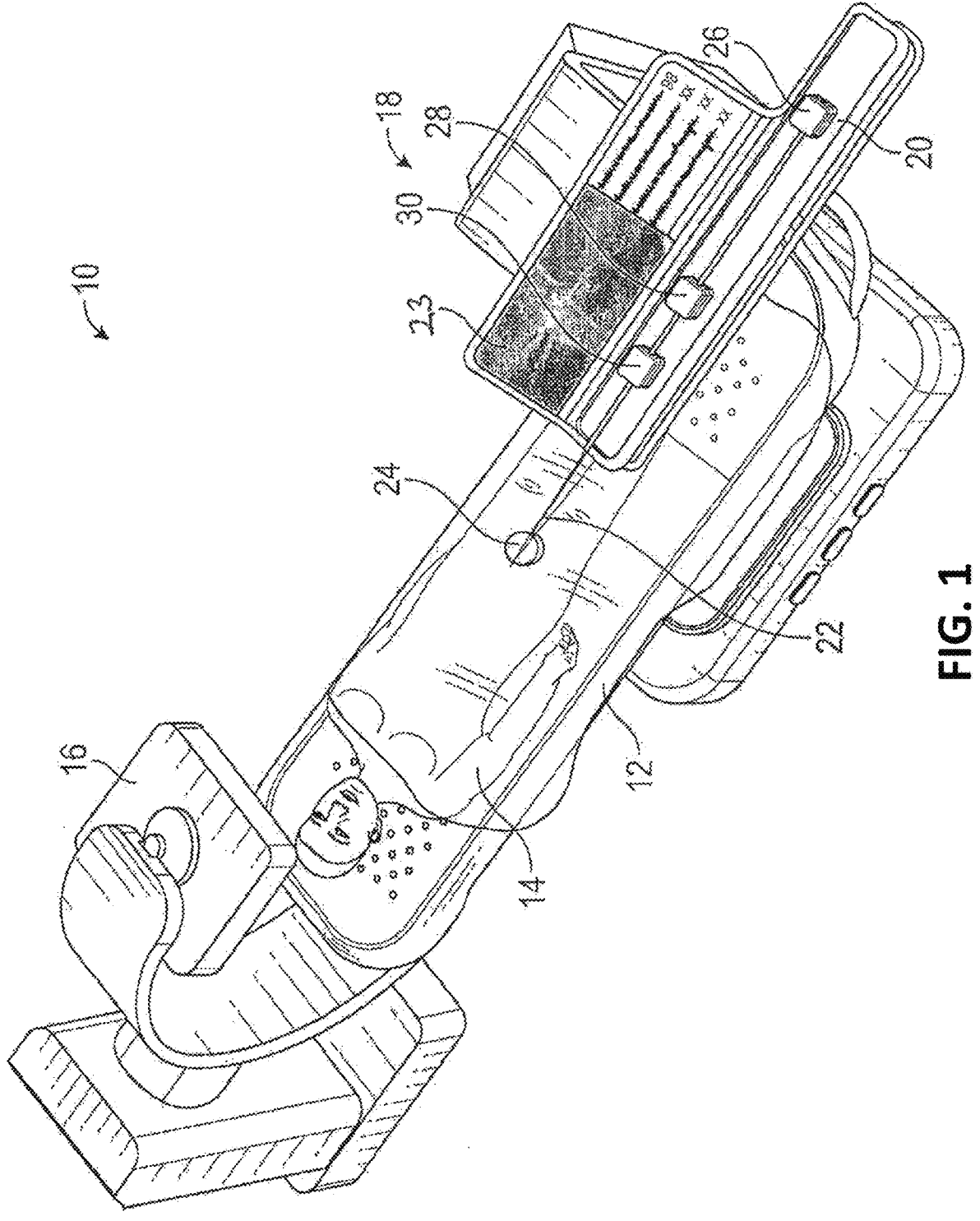
FIG. 1 is a schematic perspective view of an interventional setup having an imaging system, a patient support table, and a robotic drive system in accordance with the present invention.

FIG. 1 is a schematic perspective view of an interventional setup 10 having a patient support table 12 for supporting a patient 14. An imaging system 16 may be provided, along with a robotic interventional device drive system 18 in accordance with the present invention.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or there along, or to inject saline or contrast media or therapeutic agents.

More or fewer interventional device hubs may be provided depending upon the desired clinical procedure. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, pulmonary airways, treatment sites reached via trans ureteral or urethral or fallopian tube navigation, or other hollow organs or structures in the body.

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
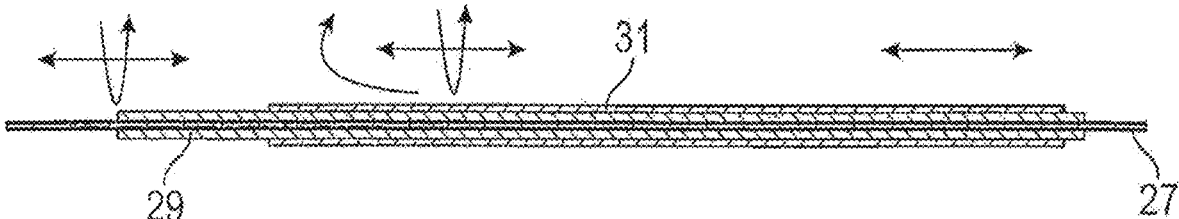
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
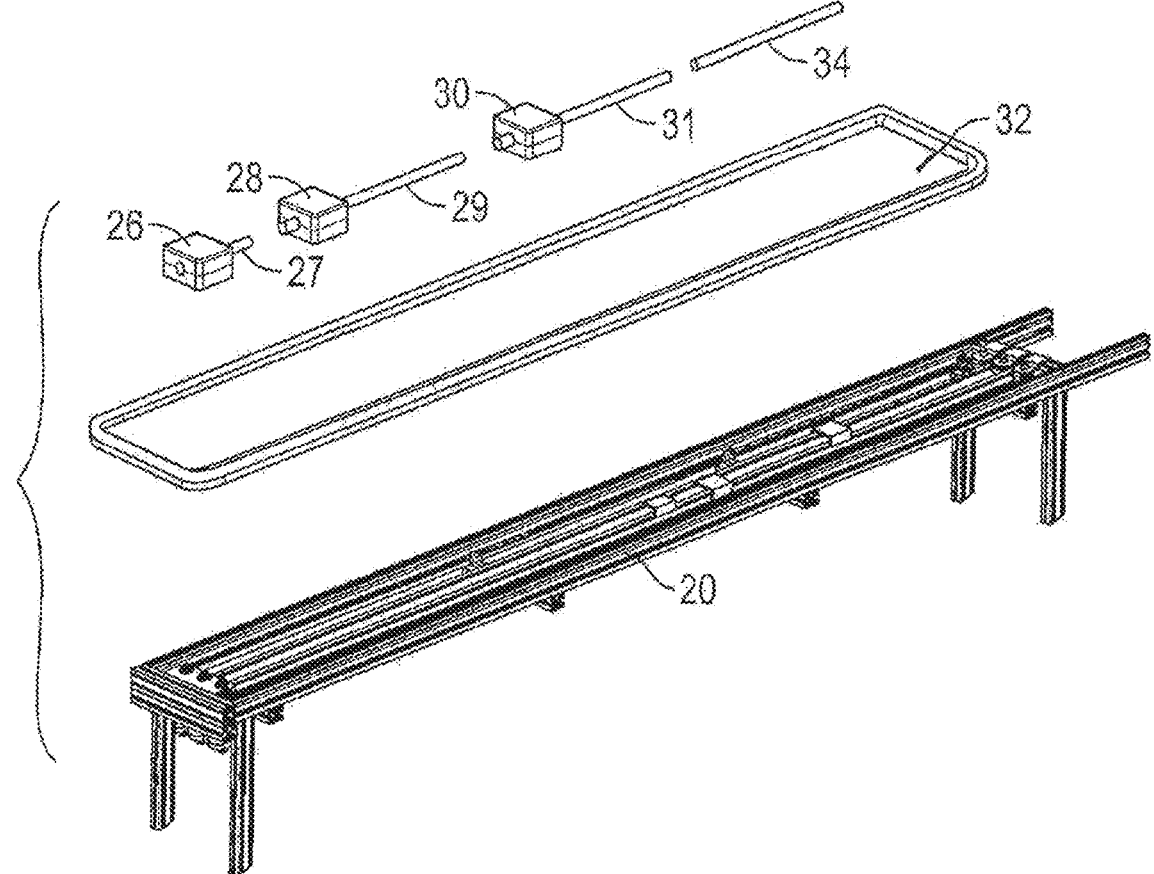
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti buckling zone for resisting buckling of the portion of the interventional devices spanning the distance between the support table 20 and the femoral artery access point 24. The anti-buckling feature 34 may comprise a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 cm or 10 cm but typically no more than about 130 cm or about 100 cm or about 50 cm or about 30 cm to support the device between the hub and the access point 24 on the patient. Reinforcement may be accomplished by embedding at least one or two or more axially extending elements into the wall, such as elongate wires or ribbons. Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, the wall thickness or diameter of the interventional device can be increased in the anti-buckling zone.

The interventional device hubs may be separated from the support table 20 by sterile barrier 32. Sterile barrier 32 may comprise a thin plastic membrane such as PET. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices.

Figure 3B:
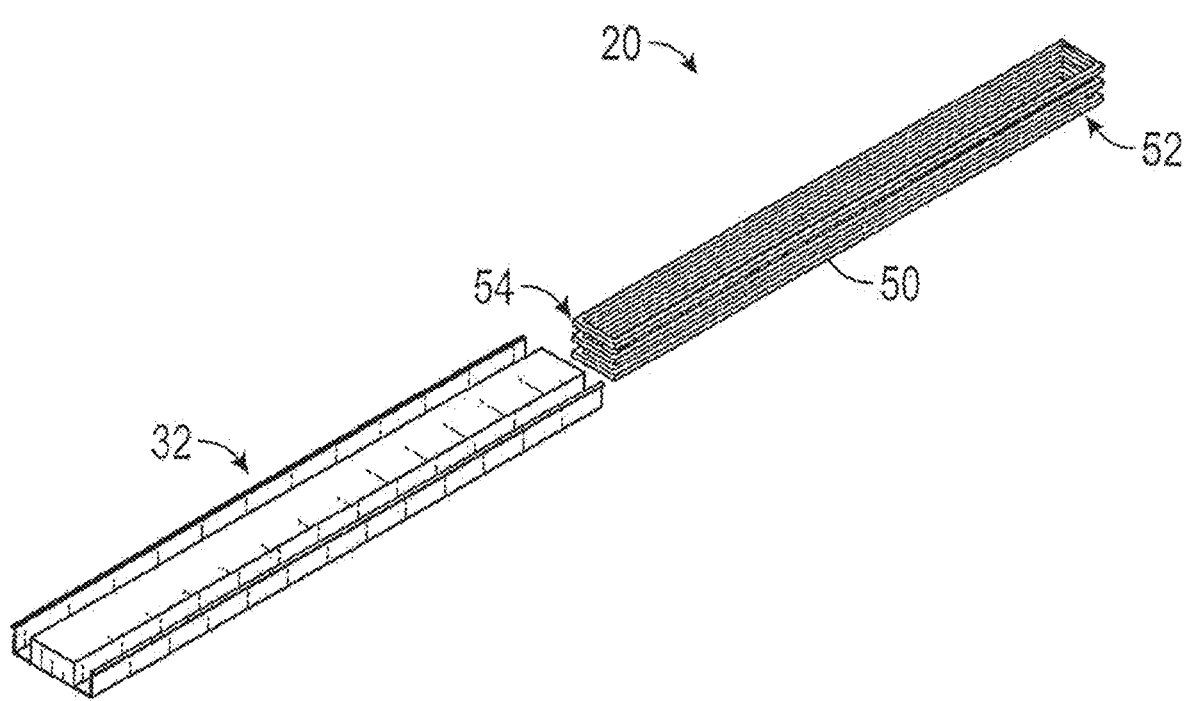
FIGS. 3B-3F Show an alternate sterile barrier in the form of a shipping tray having one or more storage channels for carrying interventional devices.
Figure 3C:
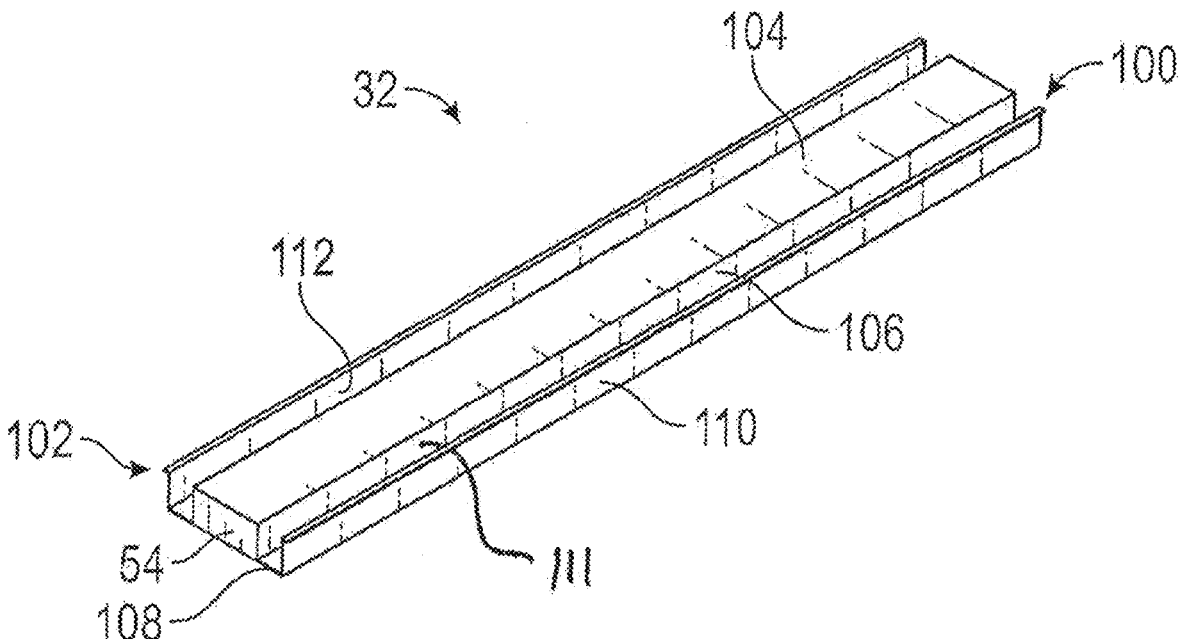

Referring to FIGS. 3B and 3C, there is illustrated a sterile barrier 32 in the form of a pre-shaped tray, for fitting over an elongate support table 20. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration. The length of support surface 104 will typically be at least about 150 cm or about 180 cm in a linear drive table. Shorter lengths may be utilized in a system configured to advance the drive couplers along an arcuate path.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs. First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure.

Figure 3D:
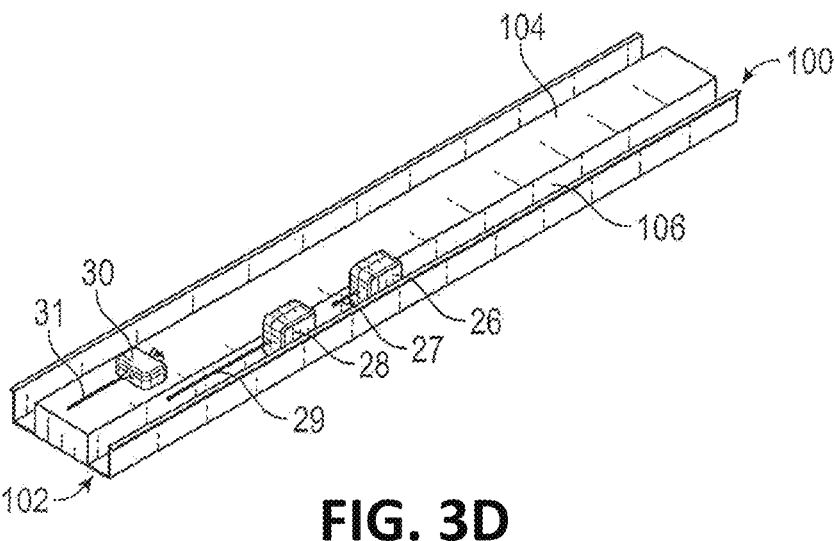

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guide wire hub 26 and guide wire 27 are illustrated residing within the first channel 106 such as before introduction through the guide catheter 31 or following removal from the guide catheter 31. The length of the catheters has been cut down to simplify the drawing.

The interventional devices may be positioned within the channel 106 and enclosed in a sterile barrier for shipping. The sterile barrier containing the sterile interventional devices may be contained within a second, outer sealed container such as a membrane pouch, which may be a second, outer sterile barrier At the clinical site, an upper panel of the sterile barrier may be removed, or an outer tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
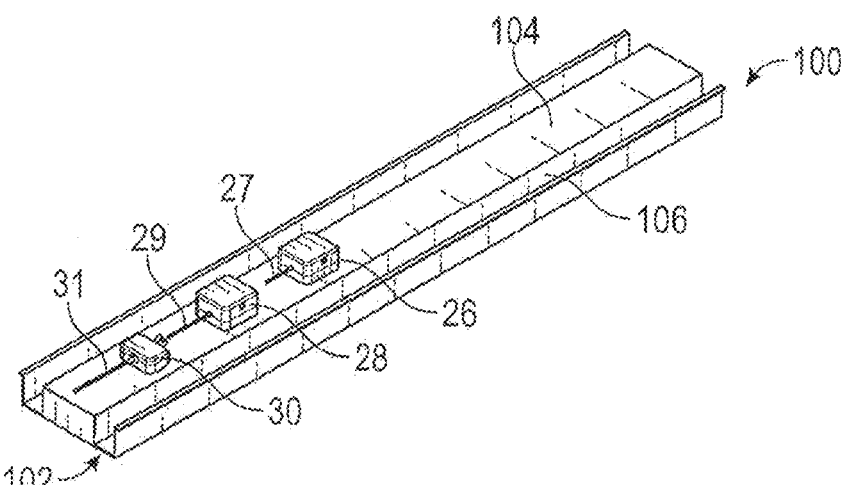
Figure 3F:
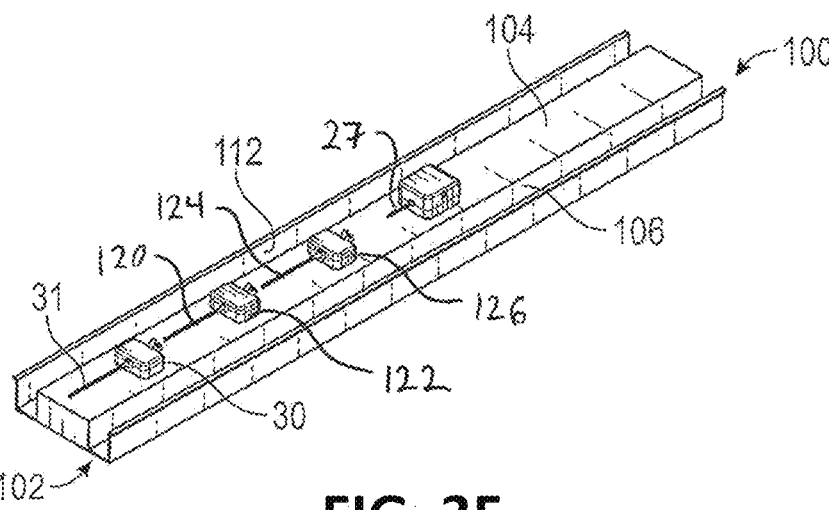

FIGS. 3D-3F illustrate the support table with sterile barrier in place, and in FIG. 3E the interventional devices configured in an access assembly for aortic access, following coupling of the access assembly to the corresponding carriages beneath the sterile barrier. The access assembly may be pre-assembled with the guidewire fully advanced through the access catheter which is in turn fully advanced through the guide catheter. This access assembly may be lifted out of the channel 106 as a unit and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guide wire hub 26 is positioned most proximally, in order to allow the guide wire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guide wire 27 extends through at least a portion of the second procedure catheter 124 in a rapid exchange version of second procedure catheter 124, or the entire length of second procedure catheter 124 in an over the wire implementation.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 4, 5A, 5B:
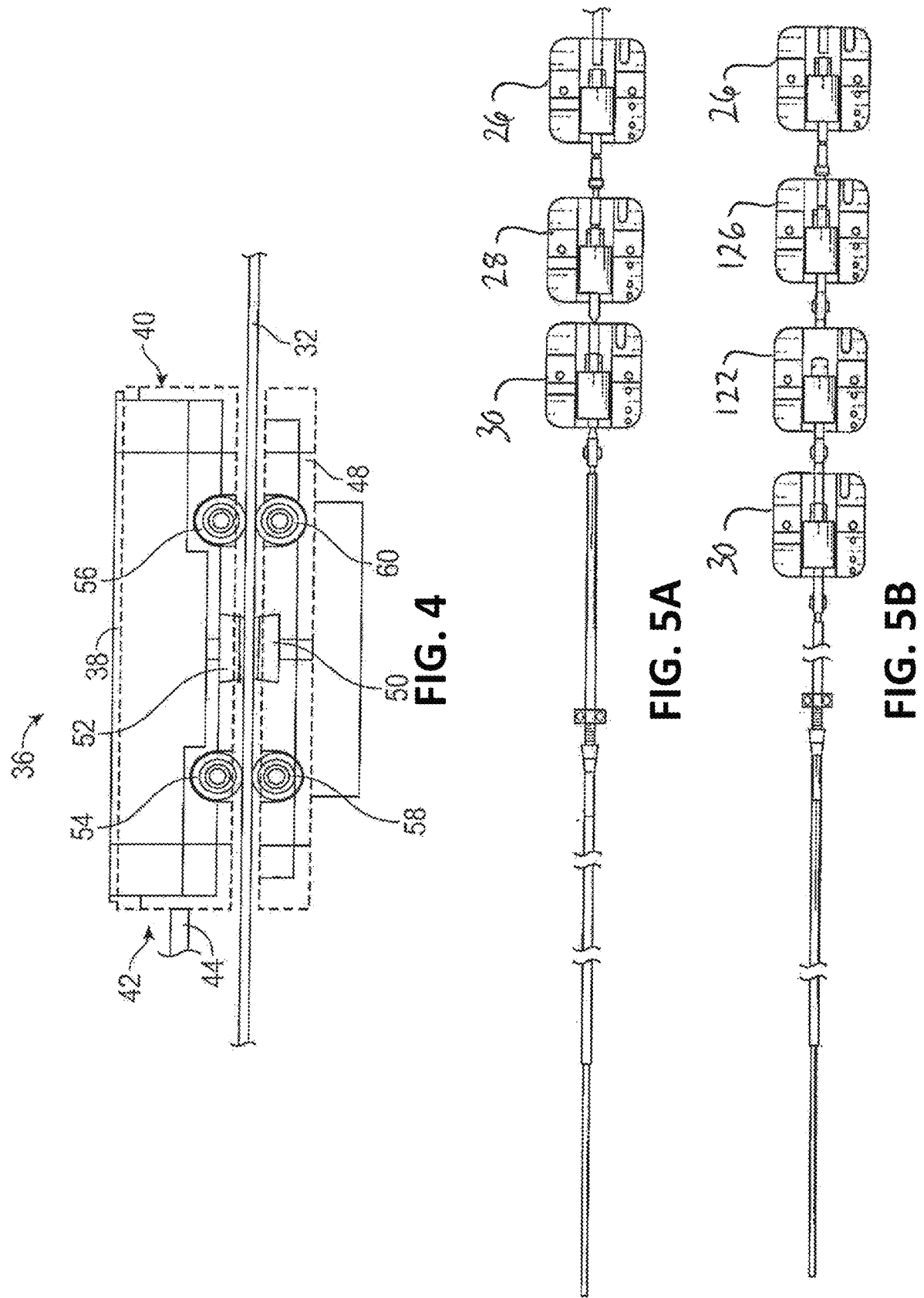
FIG. 4 is a schematic elevational cross section through a hub adapter having a drive magnet separated from an interventional device hub and driven magnet by a sterile barrier.
FIGS. 5A and 5B schematically illustrate a three interventional device and a four interventional device assembly.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions. The hub adapter 48 includes at least one drive magnet 50 configured to couple with a driven magnet 52 carried by the hub 36. This provides a magnetic coupling between the drive magnet 50 and driven magnet 52 through the sterile barrier 32 such that the hub 36 and associated interventional device is moved across the top of the sterile barrier 32 within the sterile field in response to movement of the hub adapter 48 outside of the sterile field. Movement of the hub adapter is driven by a drive system carried by the support table and described in additional detail below.

To reduce friction in the system, the hub 36 may be provided with at least a first roller 54 and a second roller 56 which may be in the form of wheels or rotatable balls or drums. The rollers space the sterile barrier 32 apart from the surface of the driven magnet 52 by at least about 0.008" and generally no more than about 0.03". In some implementations of the invention the space is within the range of from about 0.010" and about 0.016". The space between the drive magnet 50 and driven magnet 52 is generally no more than about 0.15" and in some implementations is no more than about 0.10" such as within the range of from about 0.085" to about 0.090". The hub adapter 48 may similarly be provided with at least a first hub adapter roller 58 and the second hub adapter roller 60, which may be positioned opposite the respective first roller 54 and second roller 56 as illustrated in FIG. 4.

Figure 6:
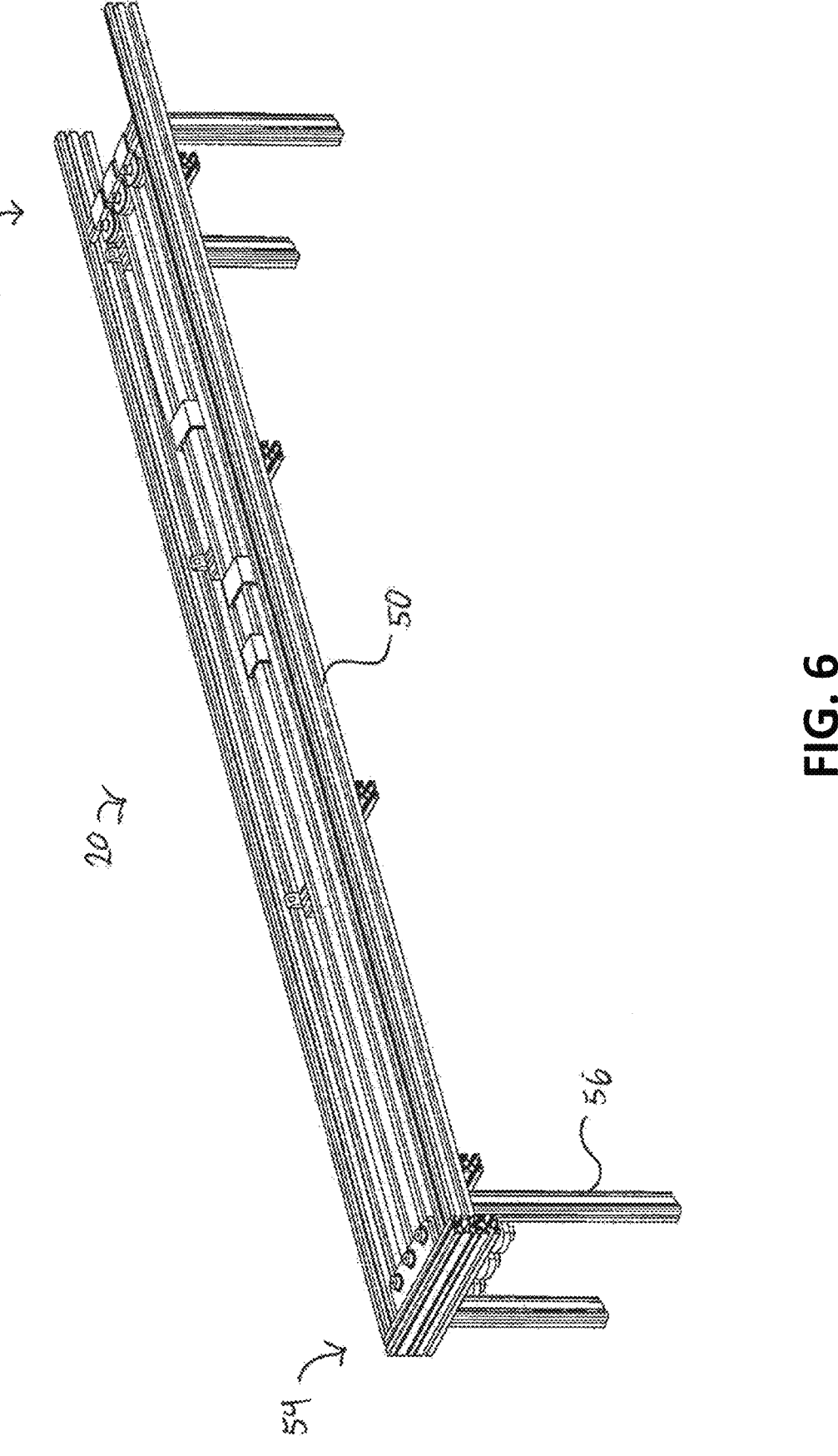
FIG. 6 is a perspective view of a support table.

Referring to FIG. 6, there is schematically illustrated one example of a low-profile linear drive support table 20. Support table 20 comprises an elongated frame 50 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 50 over or adjacent to the patient.

Figure 7:
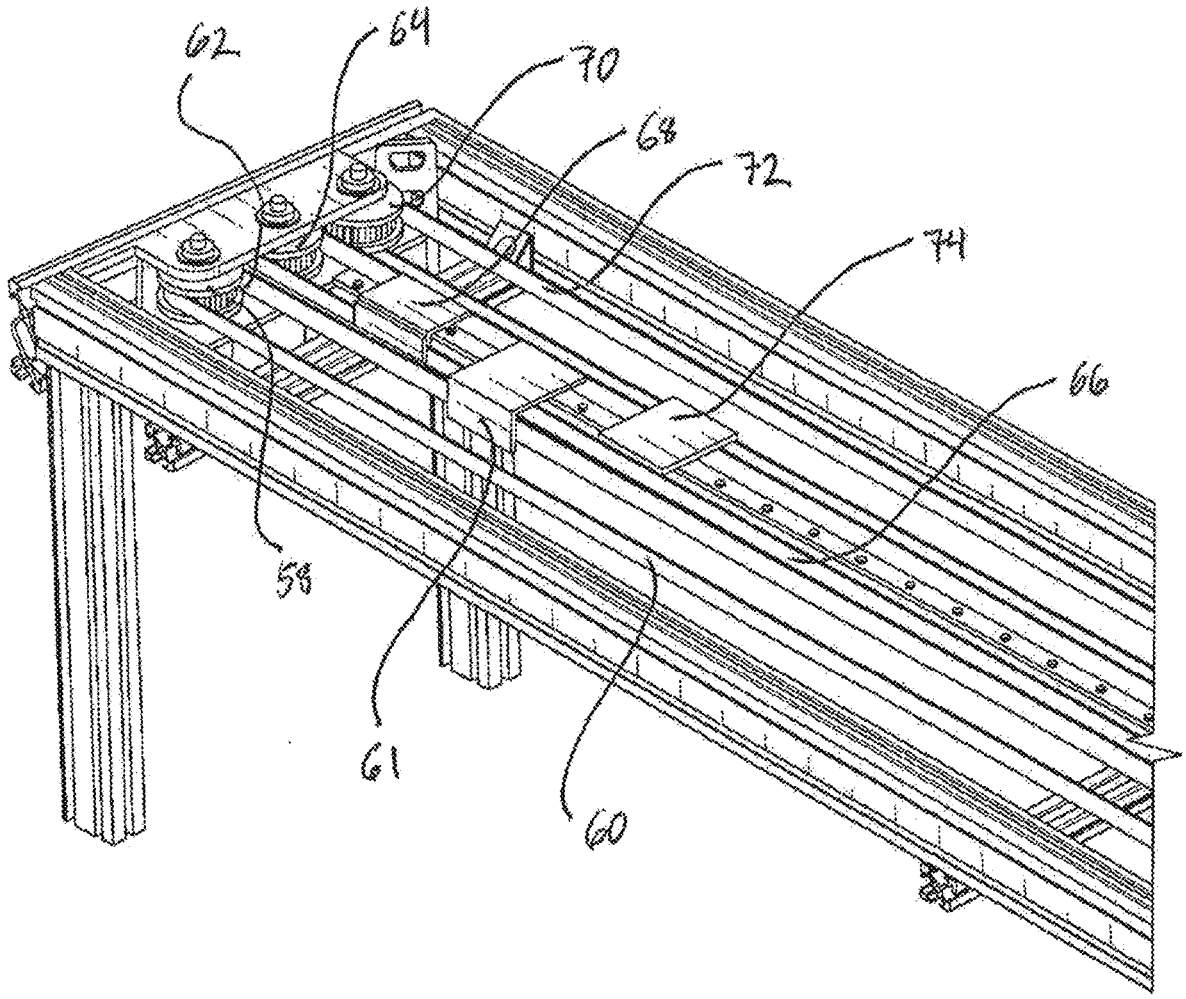
FIG. 7 is a close-up view of the motor drive end of a support table.

One example of a linear drive table 20 illustrated in FIG. 7 includes three distinct drives. However, two drives or four or more drives may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 74 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
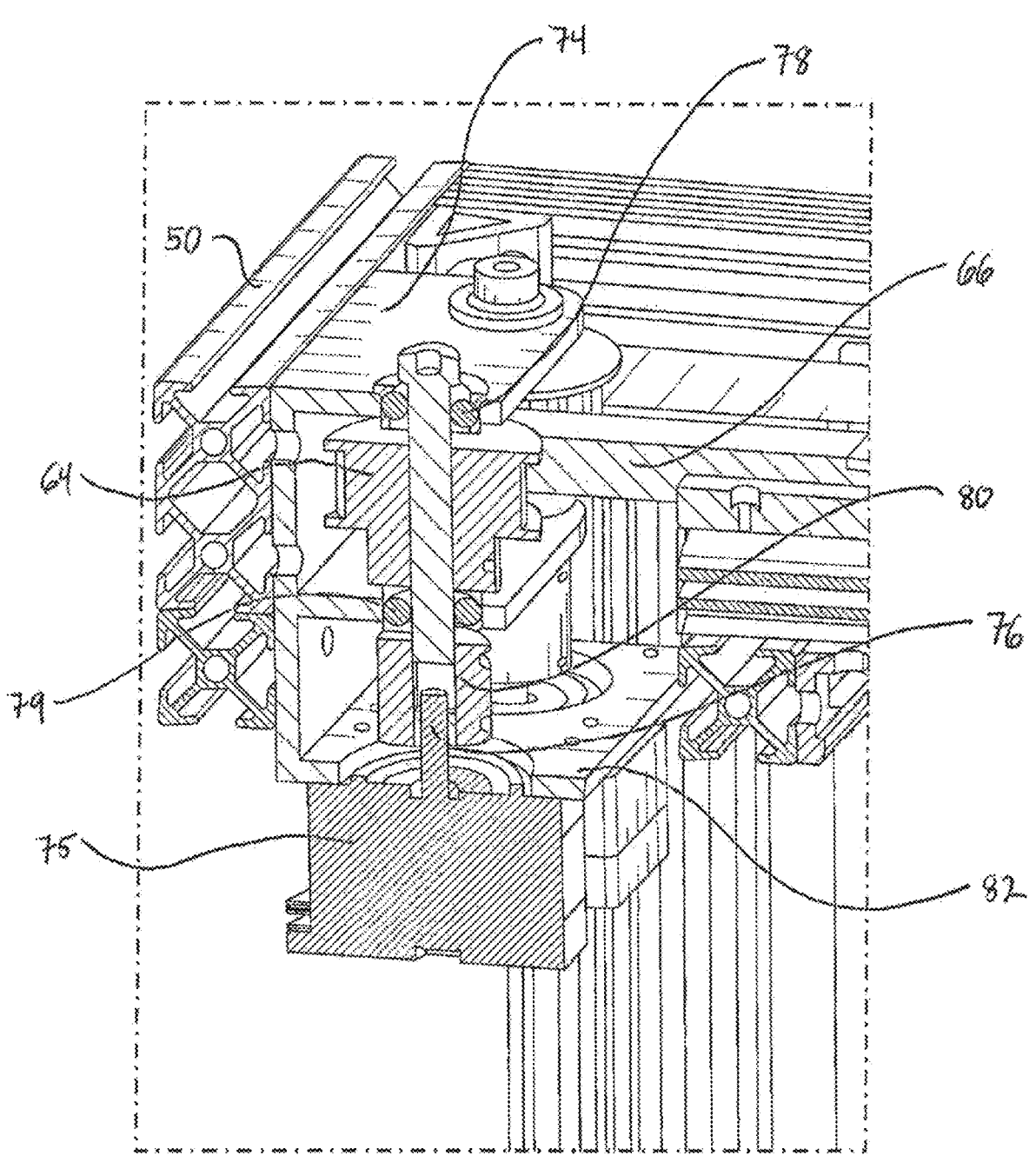
FIG. 8 is an elevational cross section through a motor and belt drive assembly.

A detail view of a drive system is shown schematically in FIG. 8. A drive support 74 may be carried by the frame 50 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 50. The belt drive assemblies for the first drive belt 60 and third drive belt 72 maybe similarly constructed and are not further detailed herein.

Figure 9:
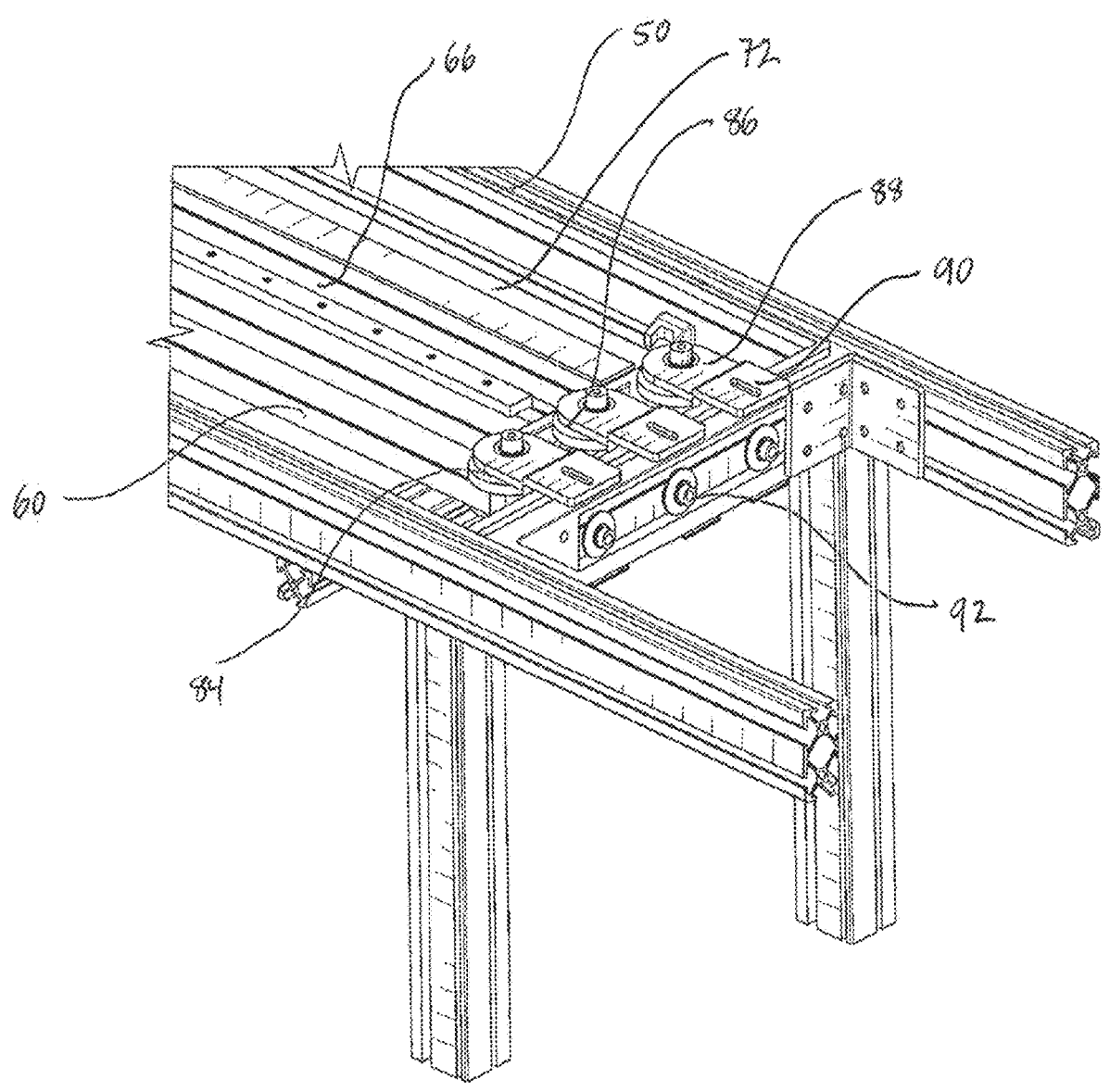
FIG. 9 is a close-up view of a pulley end of the support table.
Figure 10:
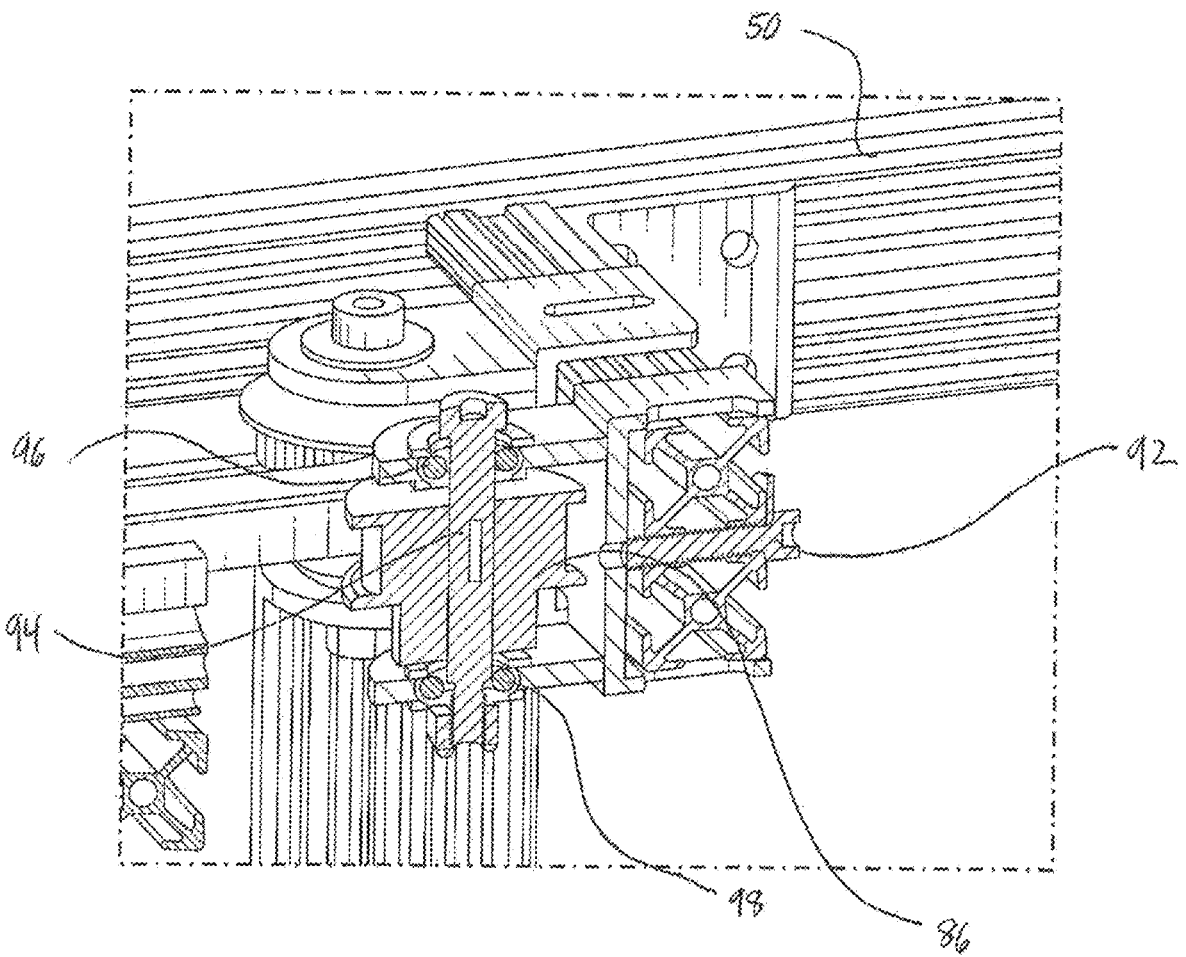
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 11:
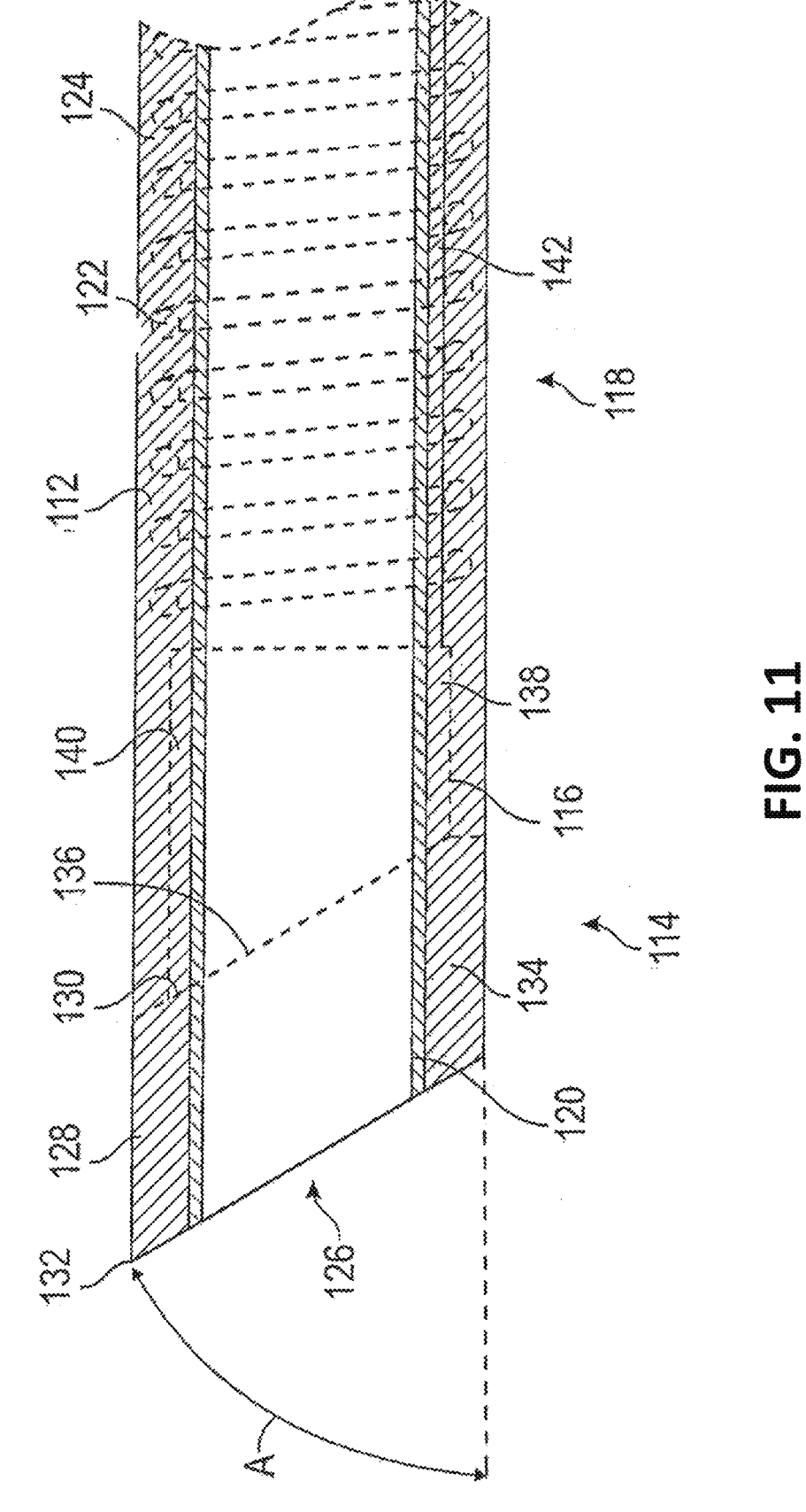
FIG. 11 is a side elevational cross-section through a distal portion of a catheter such as any of those shown in FIGS. 5A and 5B.

Any of the catheters illustrated, for example, in FIGS. 5A, 5B or 11 generally comprise an elongate tubular body extending between a proximal end and a distal functional end. The length and diameter of the tubular body depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 110 comprises a tubular body 112 which includes an advance segment 114, a marker band 116 and a proximal segment 118. An inner tubular liner 120 may extend throughout the length of the distal catheter tip 110, and may comprise dip coated PTFE.

A reinforcing element 122 such as a braid or spring coil is embedded in an outer jacket 124 which may extend the entire length of the catheter.

The advance segment 114 terminates distally in an angled face 126, to provide a leading side wall portion 128 having a length measured between the distal end 130 of the marker band 116 and a distal tip 132. A trailing side wall portion 134 of the advance segment 114, has an axial length in the illustrated embodiment of approximately equal to the axial length of the leading side wall portion 128 as measured at approximately 180 degrees around the catheter from the leading side wall portion 128. The leading side wall portion 128 may have an axial length within the range of from about 0.1 mm to about 5 mm and generally within the range of from about 1 to 3 mm. The trailing side wall portion 134 may be equal to or at least about 0.1 or 0.5 or 1 mm or 2 mm or more shorter than the axial length of the leading side wall portion 128, depending upon the desired performance.

The angled face 126 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105%, and no more than about 130%, in some implementations within the range of from about 110% and about 125% and in one example is about 115% of the area of the corresponding circular port (angle A is 90 degrees).

In the illustrated embodiment, the axial length of the advance segment is substantially constant around the circumference of the catheter, so that the angled face 126 is approximately parallel to the distal surface 136 of the marker band 116. The marker band 116 has a proximal surface approximately transverse to the longitudinal axis of the catheter, producing a marker band 116 having a right trapezoid configuration in side elevational view. A short sidewall 138 is rotationally aligned with the trailing side wall portion 134, and has an axial length within the range of from about 0.2 mm to about 4 mm, and typically from about 0.5 mm to about 2 mm. An opposing long sidewall 140 is rotationally aligned with the leading side wall portion 128. Long sidewall 140 of the marker band 116 is generally at least about 10% or 20% longer than short sidewall 138 and may be at least about 50% or 70% or 90% or more longer than short sidewall 138, depending upon desired performance. Generally, the long sidewall 140 will have a length of at least about 0.5 mm or 1 mm and less than about 5 mm or 4 mm.

The marker band may be a continuous annular structure, or may have at least one and optionally two or three or more axially extending slits throughout its length. The slit may be located on the short sidewall 138 or the long sidewall 140 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The marker band zone of the assembled catheter may have a relatively high bending stiffness and high crush strength, such as at least about 50% or at least about 100% less than proximal segment 18 but generally no more than about 200% less than proximal segment 118. The high crush strength may provide radial support to the adjacent advance segment 114 and particularly to the leading side wall portion 128, to facilitate the functioning of distal tip 132 as an atraumatic bumper during transluminal advance and to resist collapse under vacuum. The proximal segment 118 preferably has a lower bending stiffness than the marker band zone, and the advance segment 114 preferably has even a lower bending stiffness and crush strength than the proximal segment 118.

The advance segment 114 may comprise a distal extension of the outer tubular jacket 124 and optionally the inner liner 120, without other internal supporting structures distally of the marker band 116. Outer jacket 124 may comprise extruded Tecothane. The advance segment 114 may have a bending stiffness and radial crush stiffness that is no more than about 50%, and in some implementations no more than about 25% or 15% or 5% or less than the corresponding value for the proximal segment 118.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments 142. The one or more tension element 142 may be axially placed inside the catheter wall near the distal end of the catheter. The one or more tension element 142 may serve as a tension support and resist tip detachment or elongation of the catheter wall under tension (e.g., when the catheter is being proximally retracted through a kinked outer catheter or tortuous or narrowed vasculature).

At least one of the one or more tension element 142 may proximally extend along the length of the catheter wall from within about 1.0 cm from the distal end of the catheter to less than about 10 cm from the distal end of the catheter, less than about 20 cm from the distal end of the catheter, less than about 30 cm from the distal end of the catheter, less than about 40 cm from the distal end of the catheter, or less than about 50 cm from the distal end of the catheter.

The one or more tension element 142 may have a length greater than or equal to about 40 cm, greater than or equal to about 30 cm, greater than or equal to about 20 cm, greater than or equal to about 10 cm, or greater than or equal to about 5 cm.

At least one of the one or more tension element 142 may extend at least about the most distal 50 cm of the length of the catheter, at least about the most distal 40 cm of the length of the catheter, at least about the most distal 30 cm or 20 cm or 10 cm of the length of the catheter.

In some implementations, the tension element extends proximally from the distal end of the catheter along the length of the coil 24 and ends proximally within about 5 cm or 2 cm or less either side of a transition between a distal coil and a proximal braid. The tension element may end at the transition without overlapping with the braid.

The one or more tension element 142 may be placed near or radially outside the inner liner 120. The one or more tension element 142 may be placed near or radially inside the braid and/or the coil. The one or more tension element 142 may be carried between the inner liner 120 and the helical coil, and may be secured to the inner liner or other underlying surface by an adhesive prior to addition of the next outer adjacent layer such as the coil. Preferably, the tension element 142 is secured to the marker band 116 such as by adhesives or by mechanical interference. In one implementation, the tension element 142 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 142 or filament bundles are spaced circumferentially apart in the catheter wall, the tension elements 142 may be placed in a radially symmetrical manner. For example, the angle between two tension elements 142 with respect to the radial center of the catheter may be about 180 degrees. Alternatively, depending on desired clinical performances (e.g., flexibility, trackability), the tension elements 142 may be placed in a radially asymmetrical manner. The angle between any two tension elements 142 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 142 may comprise materials such as Vectran, Kevlar, Polyester, Meta-Para-Aramide, or any combinations thereof. At least one of the one or more tension element 142 may comprise a single fiber or a multi-fiber bundle, and the fiber or bundle may have a round or rectangular (e.g. ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 142, as measured in the radial direction, may be no more than about 2%, 5%, 8%, 15%, or 20% of that of the catheter 10.

The cross-sectional dimension of the one or more tension element 142, as measured in the radial direction, may be no more than about 0.001 inches, no more than about 0.002 inches, no more than about 0.004 inches, no more than about 0.006 inches, no more than about 0.008 inches, or about 0.015 inches.

The one or more tension element 142 may increase the tensile strength of the distal zone of the catheter before failure under tension (e.g. marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
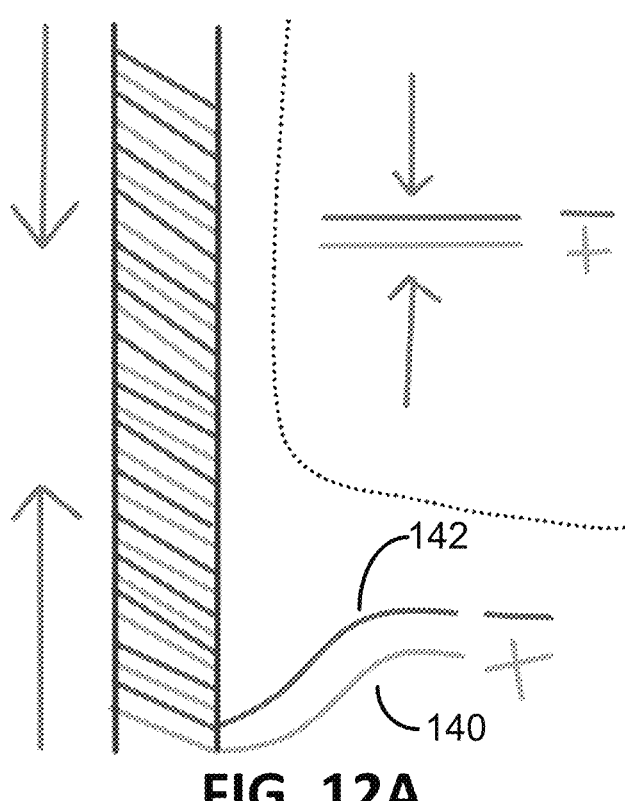
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations of the invention, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
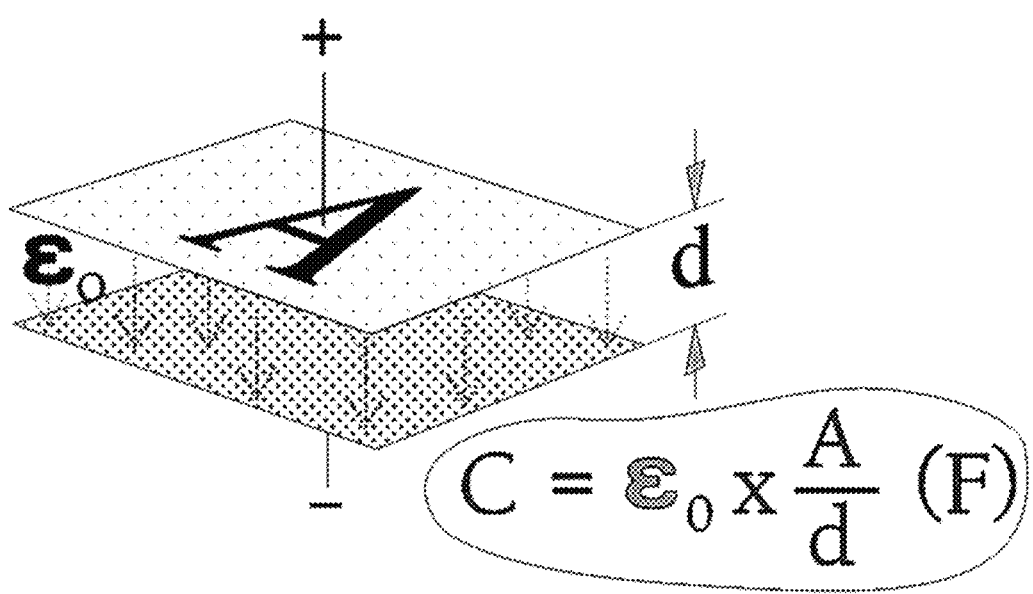

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires 140 and 142 will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 cm of the catheter body to sense forces experienced at the distal end. At least a second capacitor may be provided within the proximal most 5 or 10 or 20 cm of the catheter body, to sense forces experienced at the proximal end of the catheter.

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways.

One method for measuring the relative distance between the puck and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs carriages.

The magnetic coupling between the hub and the carriage has a break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the pucks through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board may run the entire working length of the table (e.g., at least about 5' or 6') configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. The processing may be done in real time to provide position/orientation data at up to 30 hz (the max speed of the fluoro), although this technique would only provide data while the fluoro is turned on.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders $(d\theta)$ tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path.

Figure 15:
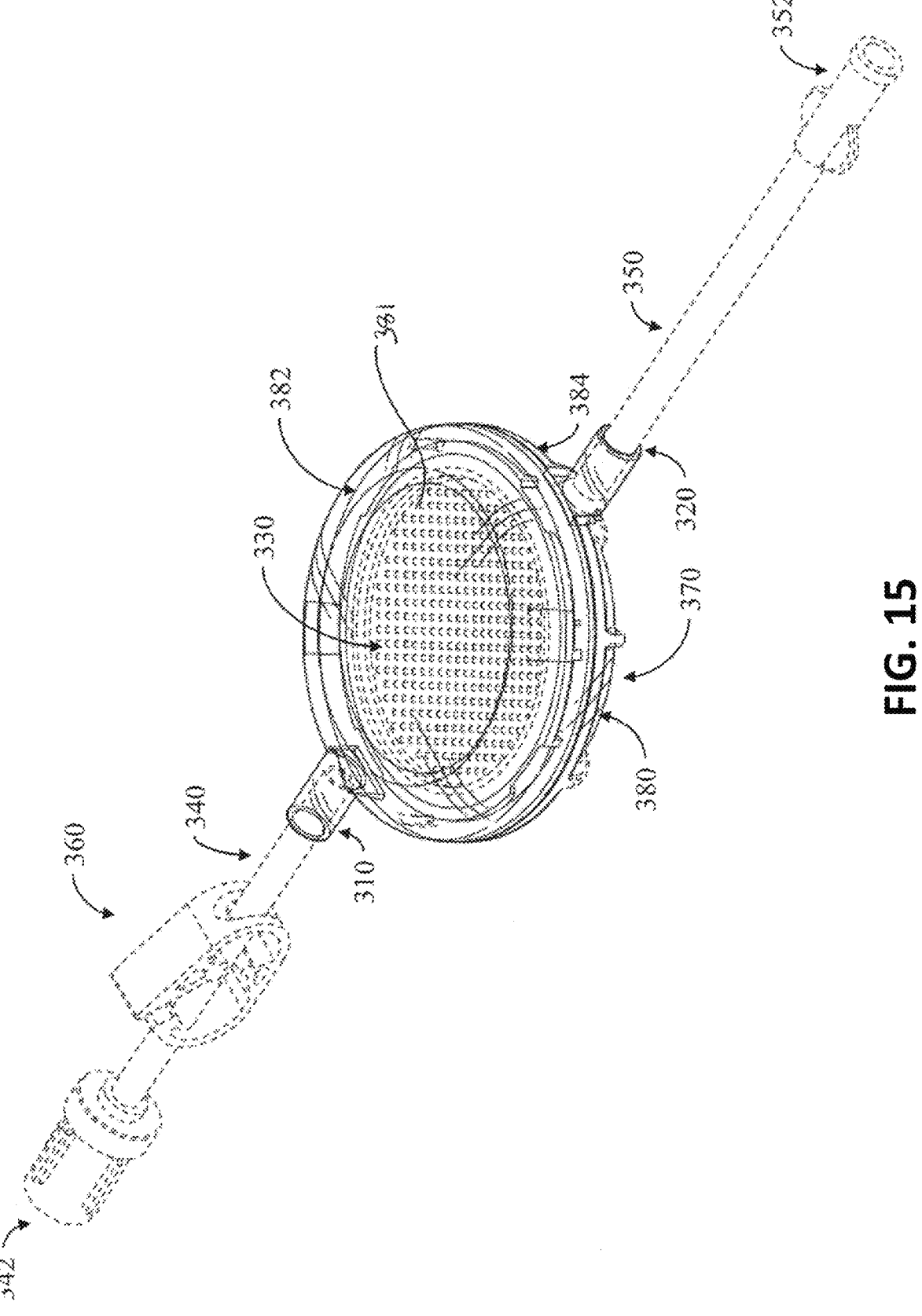
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320. In some examples, the body 380 can include a flush port (not illustrated) that is configured to allow the injection of saline or other fluid into the chamber 381 to improve clot visualization once it is trapped in the filter 330.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter. In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter. In an implementation configured for remote operation, any of a variety of sensors may be provided to detect clot passing through the aspiration line and/or trapped in the filter, such as an optical sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump. In some examples, the system 300 can include a clamp 360. The clamp 360 can be positioned over the first tube 340 to allow the user to engage the clamp and provide flow control over the clot retrieval device 370.

The body 380 can have a top surface spaced apart from a bottom surface by a tubular side wall. In the illustrated implementation, the top and bottom surfaces are substantially circular, and spaced apart by a cylindrical side wall having a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of each of which is hereby incorporated by reference herein.

The foregoing represents certain specific implementations of a drive table and associated catheters. a wide variety of different drive table constructions can be made, for supporting and axially advancing and retracting two or three or four or more drive magnet assemblies to robotically drive interventional devices, as will be appreciated by those of skill in the art in view of the disclosure herein.

EXAMPLE EMBODIMENTS

A supra-aortic vessel access robotic control system comprising one or more of the following:

a guidewire hub configured to adjust each of an axial position and a rotational position of a guidewire;

a guide catheter hub configured to adjust a guide catheter in an axial direction; and a second catheter hub configured to adjust each of an axial position and a rotational position of a second catheter, and also to laterally deflect a distal deflection zone of the second catheter.

A control system as described in any embodiment herein, wherein the second catheter is an aspiration catheter.

A control system as described in any embodiment herein, wherein the second catheter is an embolic deployment catheter.

A control system as described in any embodiment herein, wherein the second catheter is configured to deploy embolic coils.

A control system as described in any embodiment herein, wherein the second catheter is a stent deployment catheter.

A control system as described in any embodiment herein, wherein the second catheter is configured to deploy a stentriever.

A control system as described in any embodiment herein, wherein the second catheter is a flow diverter deployment catheter.

A control system as described in any embodiment herein, wherein the second catheter is a diagnostic angiographic catheter.

A control system as described in any embodiment herein, further comprising a driven magnet on the guidewire hub configured to cooperate with a drive magnet such that the driven magnet moves in response to movement of the drive magnet.

A control system as described in any embodiment herein, wherein the drive magnet is axially movably carried by a support table.

A control system as described in any embodiment herein, wherein the drive magnet moves outside of the sterile field separated from the driven magnet by a barrier, and the driven magnet is within the sterile field.

A control system as described in any embodiment herein, wherein the barrier comprises a polymer membrane.

A control system as described in any embodiment herein, further comprising a control console located remotely from the support table.

A control system as described in any embodiment herein, wherein the position of the driven magnet is movable in response to manipulation of a guidewire drive control on the console.

A control system as described in any embodiment herein, further comprising a processor for controlling the position of the driven magnet, and the processor is in wired communication with the control console.

A control system as described in any embodiment herein, further comprising a processor for controlling the position of the driven magnet, and the processor is in wireless communication with the control console.

A control system as described in any embodiment herein, wherein the driven magnet will remain engaged with the drive magnet until an applied force reaches a disruption force threshold above which the driven magnet will become decoupled from the drive magnet.

A control system as described in any embodiment herein, wherein the disruption force threshold is at least about 300 grams.

A control system as described in any embodiment herein, further comprising a sensor configured to measure the applied force between the driven magnet and the drive magnet.

A control system as described in any embodiment herein, further comprising a processor configured to compare an applied force to the disruption force threshold.

A control system as described in any embodiment herein, wherein the processor is configured to adjust a rate of movement of the drive magnet when the applied force reaches a preset value below the disruption force threshold.

A control system as described in any embodiment herein, wherein the sensor comprises a strain gauge.

A control system as described in any embodiment herein, wherein the processor is configured to halt movement of the drive magnet when the applied force reaches a preset value below the disruption force threshold.

A robotically driven interventional device comprising one or more of the following:

an elongate, flexible body, having a proximal end and a distal end;

a hub on the proximal end at least one rotatable roller on a first surface of the hub; and at least one magnet on the first surface of the hub.

A robotically driven interventional device as described in any embodiment herein, wherein the roller extends further away from the first surface than the magnet.

A robotically driven interventional device as described in any embodiment herein, further comprising at least a second roller.

A robotically driven interventional device as described in any embodiment herein, further comprising a rotational drive within the hub, for rotating the interventional device with respect to the hub.

A robotically driven interventional device as described in any embodiment herein, further comprising a retraction mechanism in the hub, for proximally retracting a pull element extending through the interventional device.

A robotically driven interventional device as described in any embodiment herein, wherein the pull element comprises a pull wire.

A robotically driven interventional device as described in any embodiment herein, wherein the pull element comprises a pull tube.

A robotically driven interventional device as described in any embodiment herein, wherein a shape of a portion of the tubular body changes in response to proximal retraction of the pull element.

A robotically driven interventional device as described in any embodiment herein, wherein a stiffness characteristic of a portion of the tubular body changes in response to proximal retraction of the pull element.

A robotically driven interventional device as described in any embodiment herein, further comprising a sensor on the elongate flexible body.

A robotically driven interventional device as described in any embodiment herein, wherein the sensor comprises an axial force sensor.

A robotically driven interventional device as described in any embodiment herein, wherein a distal portion of the flexible body includes at least a first electrical conductor spaced axially apart from and insulated from a second electrical conductor.

A robotically driven interventional device as described in any embodiment herein, wherein first electrical conductor and second electrical conductor are adjacent helical windings of conductive wire.

A robotically driven interventional device as described in any embodiment herein, wherein the sensor comprises an oxygen sensor.

A robotically driven interventional device as described in any embodiment herein, wherein the sensor comprises a catheter shape sensor.

A robotically driven interventional device as described in any embodiment herein, wherein the sensor comprises a catheter position sensor.

A robotically driven interventional device as described in any embodiment herein, wherein the flexible body comprises a guide catheter.

A robotically driven interventional device as described in any embodiment herein, wherein the flexible body comprises a guidewire.

A robotically driven interventional device as described in any embodiment herein, wherein the flexible body comprises an access catheter.

A robotically driven interventional device as described in any embodiment herein, wherein the flexible body comprises an aspiration catheter.

A robotically driven interventional device as described in any embodiment herein, comprising a fiber bragg grating sensor.

A robotically driven interventional device as described in any embodiment herein, further comprising a clot filter in fluid communication with the hub.

A robotically driven interventional device as described in any embodiment herein, wherein the clot filter is carried by the hub.

A robotically driven interventional device as described in any embodiment herein, wherein the clot filter has a transparent side wall to permit visual inspection of captured clot.

A robotically driven interventional device as described in any embodiment herein, further comprising a bubble detector in fluid communication with a flow path through the hub.

A robotically driven interventional device as described in any embodiment herein, wherein the bubble detector is carried by the hub.

A robotically driven interventional device as described in any embodiment herein, further comprising a valve in the flow path, and a processor configured to adjust the valve in response to detection of bubbles in the flow path.

A robotically driven interventional device as described in any embodiment herein, wherein bubbles are diverted out of the flow path in response to adjustment of the valve.

A sterile packaging assembly for transporting interventional devices to a robotic surgery site comprising one or more of the following:
    a sterile barrier having a hub support portion and configured to enclose a sterile volume; and
    at least a first interventional device within the sterile volume, the first interventional device including a hub and an elongate flexible body, the hub including at least one magnet and at least one roller configured to roll on the hub support portion.

A sterile packaging assembly as described in any embodiment herein, wherein the hub support portion is configured to reside on a support table adjacent a patient, with an upper surface of the hub support portion within a sterile field and a lower surface of the hub support portion outside of the sterile field.

A sterile packaging assembly as described in any embodiment herein, wherein the hub support portion is substantially horizontal when residing on the support table.

A sterile packaging assembly as described in any embodiment herein, wherein the hub support portion is inclined relative to a horizontal plane when residing on the support table.

A sterile packaging assembly as described in any embodiment herein, wherein the hub further comprises at least one fluid injection port.

A sterile packaging assembly as described in any embodiment herein, wherein the hub further comprises a wireless RF transceiver.

A sterile packaging assembly as described in any embodiment herein, further comprising a visual indicator on the hub, for indicating the presence of a clot.

A sterile packaging assembly as described in any embodiment herein, wherein the visual indicator comprises a clot collection chamber having a transparent window.

A sterile packaging assembly as described in any embodiment herein, further comprising a filter in the clot chamber.

A sterile packaging assembly as described in any embodiment herein, further comprising a sensor for detecting the presence of a clot.

A sterile packaging assembly as described in any embodiment herein, wherein the sensor comprises a pressure sensor.

A sterile packaging assembly as described in any embodiment herein, wherein the sensor comprises an optical sensor.

A sterile packaging assembly as described in any embodiment herein, wherein the hub support portion comprises an elongate polymeric membrane having a longitudinal axis.

A sterile packaging assembly as described in any embodiment herein, wherein the sterile barrier additionally comprises at least a first storage tray adjacent the hub support portion.

A sterile packaging assembly as described in any embodiment herein, comprising a first storage tray and a second storage tray adjacent the hub support portion.

A sterile packaging assembly as described in any embodiment herein, wherein the first storage tray is on a first side of the hub support portion, and the second storage tray is on a second side of the hub support portion.

A sterile packaging assembly as described in any embodiment herein, comprising a first storage tray and a second storage tray adjacent the hub support portion.

A sterile packaging assembly as described in any embodiment herein, wherein the first interventional device is contained within the first storage tray.

A sterile packaging assembly as described in any embodiment herein, wherein the first interventional device is a guide catheter.

A sterile packaging assembly as described in any embodiment herein, wherein the first interventional device is an access catheter.

A sterile packaging assembly as described in any embodiment herein, wherein the first interventional device is a guidewire.

A sterile packaging assembly as described in any embodiment herein, wherein the first interventional device is an aspiration catheter.

A sterile packaging assembly as described in any embodiment herein, comprising a supra-aortic vessel access assembly in the first storage tray.

A sterile packaging assembly as described in any embodiment herein, wherein the access assembly comprises a guidewire, an access catheter and a guide catheter.

A sterile packaging assembly as described in any embodiment herein, further comprising a procedure assembly within the sterile volume.

A sterile packaging assembly as described in any embodiment herein, wherein the procedure assembly comprises a guidewire and an aspiration catheter.

A sterile packaging assembly as described in any embodiment herein, wherein the procedure assembly is carried in a second storage tray.

A sterile packaging assembly as described in any embodiment herein, wherein the sterile barrier is magnetically permeable.

A sterile packaging assembly as described in any embodiment herein, wherein the sterile barrier is fluid impermeable.

A sterile packaging assembly as described in any embodiment herein, wherein the sterile barrier is radiofrequency permeable.

A sterile packaging assembly as described in any embodiment herein, wherein the sterile barrier is impermeable to microorganisms.

A sterile packaging assembly as described in any embodiment herein, wherein the sterile barrier is translucent.

A sterile packaging assembly as described in any embodiment herein, wherein the sterile barrier is transparent.

A sterile packaging assembly as described in any embodiment herein, wherein the hub support portion has a convex curvature such that fluid is configured to flow away from the hub support portion.

A sterile packaging assembly as described in any embodiment herein, wherein the hub support portion has a longitudinal axis and a transverse axis and the hub support portion is convex in an upward direction in the transverse axis.

A sterile packaging assembly as described in any embodiment herein, wherein the sterile barrier is contained within an outer packaging.

A sterile packaging assembly as described in any embodiment herein, wherein the sterile barrier comprises a non-compliant polymer.

A sterile packaging assembly as described in any embodiment herein, wherein the non-compliant polymer comprises Polyethylene terephthalate (PET) or a thermoplastic polyurethane.

A sterile packaging assembly as described in any embodiment herein, wherein the sterile barrier further comprises a removable cover portion that cooperates with the hub support portion to define the sterile volume.

A sterile packaging assembly as described in any embodiment herein, wherein the hub is releasably coupled to the hub support portion via the at least one magnet.

A method of performing a neurovascular procedure comprising one or more of the following steps:

providing an access catheter having an access catheter hub;

coupling the access catheter hub to a hub adapter, movably carried by a support table;

driving the access catheter in response to movement of the hub adapter along the table until the access catheter is positioned to achieve supra-aortic vessel access;

removing the access catheter and access catheter hub from the hub adapter; and coupling a procedure catheter hub having a procedure catheter to the hub adapter.

A method as described in any embodiment herein, further comprising advancing the procedure catheter hub to position a distal end of the procedure catheter at a neurovascular treatment site.

A method as described in any embodiment herein, wherein the driving the access catheter step comprises driving the access catheter distally through a guide catheter.

A method as described in any embodiment herein, wherein the driving the access catheter step includes the step of laterally deflecting a distal region of the access catheter to achieve supra-aortic vessel access.

A method as described in any embodiment herein, wherein the coupling step comprises magnetically coupling the access catheter hub to the hub adapter.

A method as described in any embodiment herein, wherein the access catheter hub and the hub adapter are separated by a sterile field barrier.

A method as described in any embodiment herein, further comprising coupling a guide catheter hub to a guide catheter adapter through the sterile barrier.

A method as described in any embodiment herein, further comprising coupling a guidewire hub to a guidewire adapter through the sterile barrier.

A method as described in any embodiment herein, further comprising axially moving a guidewire attached to the guidewire hub in response to axially moving the guidewire adapter.

A method as described in any embodiment herein, further comprising rotating the guidewire relative to the guidewire hub.

A method as described in any embodiment herein, wherein the procedure catheter comprises an aspiration catheter.

A method as described in any embodiment herein, further comprising the step of aspirating a clot.

A method as described in any embodiment herein, further comprising driving the access catheter in response to movement of the hub adapter along the table until the access catheter achieves supra-aortic vessel access.

A method as described in any embodiment herein, further comprising maintaining supra-aortic vessel access while removing the access catheter.

A method as described in any embodiment herein, further comprising maintaining supra-aortic vessel access while coupling a procedure catheter hub.

A method as described in any embodiment herein, wherein the coupling step comprises coupling at least a first magnet on the access catheter hub to a second magnet on the hub adapter to form a magnetic coupling.

A method as described in any embodiment herein, further comprising the step of measuring elastic force across the magnetic coupling.

A method as described in any embodiment herein, further comprising the step of determining force applied to the access catheter.

A method as described in any embodiment herein, wherein the determination of force is accomplished using an optical fiber embedded in a side wall of the catheter.

A method as described in any embodiment herein, further comprising the step of determining the location of the hub adapter relative to the table.

A method of performing a neurovascular procedure, comprising one or more of the following steps:

providing an access assembly comprising a guidewire, access catheter and guide catheter;

coupling the access assembly to a robotic drive system;

driving the access assembly to achieve supra-aortic vessel access;

decoupling the guide wire and the access catheter from the access assembly;

providing a procedure assembly comprising at least a guidewire and a procedure catheter;

coupling the procedure assembly to the robotic drive system; and performing a neurovascular procedure using the procedure assembly.

A method as described in any embodiment herein, wherein the coupling the access assembly comprises magnetically coupling a hub on each of the guidewire, access catheter and guide catheter, to separate corresponding drive magnets independently movably carried by a drive table.

A method as described in any embodiment herein, wherein the coupling the access assembly to a robotic drive system is accomplished without direct contact between the access assembly and the robotic drive system.

A method as described in any embodiment herein, wherein the procedure assembly comprises a first procedure catheter and a second procedure catheter.

A method as described in any embodiment herein, wherein the guidewire and first procedure catheter are positioned concentrically within the second procedure catheter.

A method as described in any embodiment herein, wherein the procedure assembly is advanced as a unit through at least a portion of the length of the guide catheter.

A method as described in any embodiment herein, wherein the procedure comprises a neurovascular thrombectomy.

A method as described in any embodiment herein, comprising axially advancing or retracting the guidewire.

A method as described in any embodiment herein, comprising rotating the guidewire with respect to a guidewire hub.

A method as described in any embodiment herein, comprising axially advancing or retracting the access catheter.

A method as described in any embodiment herein, comprising rotating the access catheter with respect to an access catheter hub.

A method as described in any embodiment herein, comprising laterally deflecting a deflection zone on the access catheter.

A method as described in any embodiment herein, wherein the hub on each of the guidewire, access catheter and guide catheter are separated from the corresponding drive magnets by a sterile field barrier.

A method as described in any embodiment herein, wherein driving the access assembly comprises rolling the hub on each of the guidewire, access catheter and guide catheter along the sterile field barrier in response to movement of the drive magnets.

A method as described in any embodiment herein, further comprising maintaining supra-aortic vessel access while decoupling at least one of the guide wire and the access catheter from the access assembly.

A method as described in any embodiment herein, further comprising maintaining supra-aortic vessel access while coupling the procedure assembly.

A method as described in any embodiment herein, further comprising determining relative movement between a magnet in a hub and a corresponding magnet carried by the drive table.

A method as described in any embodiment herein, further comprising determining the location of the hub relative to the drive table.

A method as described in any embodiment herein, further comprising determining axial force applied to the access catheter.

A method as described in any embodiment herein, further comprising determining rotational torque applied to the access catheter.

What is claimed is:

1. A method of performing a procedure, comprising the steps of: providing an access assembly comprising a guidewire coupled to a guidewire hub, an access catheter coupled to an access catheter hub, and a guide catheter coupled to a guide catheter hub; coupling the access assembly to a robotic drive system; wherein coupling the access assembly comprises magnetically coupling the guidewire hub, the access catheter hub, and the guide catheter hub to separate corresponding drive magnets independently movably carried by a drive table;

advancing the guidewire hub, the access catheter hub, and the guide catheter hub along a support surface of the robotic drive system to achieve supra-aortic vessel access with the guidewire, the access catheter, and the guide catheter; decoupling the guidewire and the access catheter from the robotic drive system while maintaining supra-aortic vessel access with the guide catheter; providing a procedure assembly comprising a plurality of interventional devices, wherein the plurality of interventional devices comprises a procedure catheter; coupling the procedure assembly to the robotic drive system while maintaining supra-aortic vessel access with the guide catheter; advancing the procedure assembly through the guide catheter; and performing a neurovascular procedure using the procedure assembly.

2. The method as in claim 1, wherein coupling the access assembly to the robotic drive system is accomplished without direct contact between the access assembly and the robotic drive system.

3. The method as in claim 1, wherein the procedure catheter is a first procedure catheter, the procedure assembly further comprising a second procedure catheter.

4. The method as in claim 3, wherein the procedure assembly further comprises a procedure assembly guidewire, wherein the procedure assembly guidewire and the first procedure catheter are positioned concentrically within the second procedure catheter.

5. The method as in claim 4, wherein the procedure assembly is advanced as a unit through at least a portion of a length of the guide catheter.

6. The method as in claim 1, wherein the procedure comprises a neurovascular thrombectomy.

7. The method as in claim 1, comprising axially advancing or retracting the guidewire in response to movement of at least one of the drive magnets.

8. The method as in claim 7, comprising rotating the guidewire with respect to the guidewire hub.

9. The method as in claim 1, comprising axially advancing or retracting the access catheter in response to movement of at least one of the drive magnets.

10. The method as in claim 9, comprising rotating the access catheter with respect to the access catheter hub.

11. The method as in claim 10, further comprising determining rotational torque applied to the access catheter.

12. The method as in claim 9, comprising laterally deflecting a deflection zone on the access catheter.

13. The method as in claim 9, further comprising determining axial force applied to the access catheter.

14. The method as in claim 1, wherein the guidewire hub, the access catheter hub, and the guide catheter hub are separated from the corresponding drive magnets by a sterile field barrier.

15. The method as in claim 14, wherein advancing the guidewire hub, the access catheter hub, and the guide catheter hub along the support surface of the robotic drive system comprises rolling the guidewire hub, the access catheter hub, and the guide catheter hub along the sterile field barrier in response to movement of the drive magnets.

16. The method as in claim 1, further comprising determining relative movement between a magnet in a hub and a corresponding magnet carried by the drive table.

17. The method as in claim 1, further comprising determining a location of each of the guidewire hub, the access catheter hub, and the guide catheter hub relative to the drive table.

18. The method as in claim 1, wherein the guidewire hub, the access catheter hub, and the guide catheter each comprise rollers configured to roll along the support surface.

19. The method as in claim 1, wherein advancing the guidewire hub, the access catheter hub, and the guide catheter along the support surface of the robotic drive system comprises rotating rollers coupled to the guidewire hub, the access catheter hub, and the guide catheter hub.

* * * * *